(12) United States Patent
Thacker et al.

(10) Patent No.: US 7,358,044 B2
(45) Date of Patent: Apr. 15, 2008

(54) PROPHYLACTIC AND THERAPEUTIC BENEFITS OF A NEW CLASS OF IMMUNE STIMULATING PEPTIDES

(75) Inventors: James D. Thacker, Marietta, OH (US); J. Peter Fuhrer, Dayton, OH (US); Kenneth O. Willeford, Starkville, MS (US)

(73) Assignee: Argyll Biotechnologies, LLC., LaJolla, CA (US)

( * ) Notice: Subject to any disclaimer, the term of this patent is extended or adjusted under 35 U.S.C. 154(b) by 179 days.

(21) Appl. No.: 10/825,603

(22) Filed: Apr. 16, 2004

(65) Prior Publication Data

US 2005/0042635 A1    Feb. 24, 2005

Related U.S. Application Data

(60) Provisional application No. 60/463,042, filed on Apr. 16, 2003.

(51) Int. Cl.
*C12Q 1/68* (2006.01)
*A61K 38/17* (2006.01)

(52) U.S. Cl. ................. 435/6; 435/69.1; 530/350

(58) Field of Classification Search ............ None
See application file for complete search history.

(56) References Cited

U.S. PATENT DOCUMENTS 6,875,738 B1 *  4/2005  Clark-Lewis et al. .......... 514/2
6,946,445 B1 *  9/2005  Clark-Lewis et al. ......... 514/15
2002/0165123 A1 * 11/2002  Tudan et al. .................. 514/2

OTHER PUBLICATIONS

Ngo et al., 1994, The Protein Folding Problem and Tertiary Structure Prediction, pp. 492-495.*

* cited by examiner

*Primary Examiner*—Christina Chan
*Assistant Examiner*—Yunsoo Kim
(74) *Attorney, Agent, or Firm*—Novak Druce & Quigg LLP

(57) ABSTRACT

A new class of lipopeptides has been surprisingly discovered from mammalian serum that are potent immunoregulators, hereinafter, referred to as Immune Cell Potentiating Factors ("ICPF"s). The clinical and laboratory data show a wide range of prophylactic and therapeutic applications for the ICPFs including primary and adjunctive therapy in the treatment of diseases of both bacterial and viral origin as well as certain neoplastic diseases. Described herein are chemical structures of ICPF of the invention, the likely mode of action, and the surprisingly broad spectrum of therapeutic efficacy and wide margin of safety to the host species.

34 Claims, 18 Drawing Sheets

A

B

PROPHYLACTIC AND THERAPEUTIC BENEFITS OF A NEW CLASS OF IMMUNE STIMULATING PEPTIDES

Reference to Related Applications

This application claims priority to United States Provisional Application No. 60/463,042 entitled "Immune Stimulating Peptides" filed Apr. 16, 2003, the entirety of which is hereby incorporated by reference.

BACKGROUND OF THE INVENTION

1. Field of the Invention

The invention is directed to a new class of immune stimulating peptides. In particular, the invention is directed to methods of obtaining these peptides from mammalian serum and to methods of administering these peptides for the therapeutic or prophylactic treatment of viral and infectious diseases and cancer.

2. Description of the Background

Discovering agents that potentiate the immune response is a driving force in modern drug research. Bioactive peptides, such as cytokines, chemokines, and cationic peptides, are classes of "relatively" low molecular weight compounds that have shown promise in this area of research. At least nine immuno-defense peptide products are commercially available with annual sales of over $4 billion (Latham, 1999).

The concept of immunostimulation originated in 1907, when William B. Coley noted spontaneous tumor regression in some patients after an episode of septicemia (Rush and Flaminio, 2000). In human and veterinary medicine, immunostimulant preparations are used primarily for treatment of chronic viral or bacterial infections. In some instances, immunostimulants have demonstrated efficacy as primary or adjunct treatment of neoplastic conditions (Rush, 2001). The proposed mechanism of action of nonspecific immunostimulant preparations is macrophage activation and subsequent release of cytokines that enhance the immune response (Rush and Flaminio, 2000). Prophylactic administration of immunostimulant preparations prior to pathogen exposure can decrease morbidity and mortality associated with acute infection (Rush, 2001).

In human medicine, immunoregulator preparations have progressed from crude microbial, viral, plant, and thymic extracts to synthetic viral complexes and chemically defined drugs (e.g., recombinant cytokines). The crude extract preparations induce nonspecific immunoregulatory activity via a generalized macrophage activation. The new generation of immunoregulators, such as the recombinant cytokines, have selective effects on particular components of the immune system (Rush, 2001).

Because cells of the immune system circulate through the blood and lymphatic system, serum is a logical place to look for immunoregulators. To date, only about half of the over 100 serum proteins have been isolated and characterized (de Gruyter, 1997), leaving a variety of proteins and peptides as potential immunoregulators. For example, Caprine Serum Fraction Immunomodulator (CSFI) is a non-adjuvanted immunostimulant derived from goat serum (Ansley, Daniel R. *Composition and Method for Immunostimulation in Mammals*, U.S. Pat. No. 5,219,578; Jun. 15, 1993). CSFI is ill-defined by Ansley but is said to be composed of a mixture of serum proteins and peptides, 67% of which is immunoglobulin. In that patent Ansley describes a method for collecting the immunoglobulin containing fraction of goat serum from non-immunogenicly challenged goats. That process consisted of precipitation with sodium sulfate followed by dialysis of the re-suspended precipitate in a 30,000 dalton MW cut-off dialysis membrane to remove salts and other low molecular weight substances. The dialyzed fraction was then shown to be efficacious in the treatment of a wide variety of animal diseases including equine lower respiratory disease, ovine footrot, bovine shipping fever, bovine respiratory disease, canine lymphoma, bovine lymphoma, and canine parvovirus.

Hamm recently established evidence that this immunoglobulin containing fraction of goat serum could be used as an adjunct to conventional antibiotics in the treatment of equine lower respiratory disease. In that study more than twice as many horses (86%) were able to recover in a three week period when the treatment was augmented with the caprine serum fraction as compared to the control group (35%) that only received antibiotic treatment (Hamm, 2002). This fraction is now marketed in the U.S. under the trade name PulmoClear™ for the treatment of equine lower respiratory disease.

Some immunoregulators derived from one species appear to provide a short-term immunity from pathogenic infections when administered to a different host species. In a recent study, Willeford was able to establish that a fraction of caprine serum, substantially free of immunoglobulins, could confer significant protection to chickens challenged with a lethal dose of *Pasteurella multocida* when the caprine serum fraction was administered 24 hours prior to the bacterial challenge (Willeford, 2000). Similar results were noted by Parker in mice challenged with *Salmonella typhimurium* (Parker, 2002).

Immunoregulators have been derived from sources other than animal serum as well. For instance, a variety of immuno-stimulants have been derived from mycobacterial products (Ford, 1986; Werner and Zerial, 1984; Diasio and LoBuglio, 1995). Regressin-V, an emulsion of mycobacterial cell wall fragments, is licensed for the treatment of a variety of neoplasias in animals. A killed suspension of *Propiobacterium acnes*, Immunoregulin, is licensed for veterinary use in advanced neoplasia as an adjunct to other therapies. Although these products are capable of stimulating the immune system in animals in a non-specific manner and are therapeutically efficacious, they have also been observed to initiate untoward effects such as fever and allergic reactions that arise from the broad spectrum of the immune stimulating action (Kruth, 1998).

Immunoregulators can be divided into three main groups: (a) immuno-suppressive agents; (b) immuno-stimulating agents (e.g., *bacillus* Calmette-Guérin vaccine); and (c) the remaining immunoregulators, which include biological response modifiers (e.g., colony stimulating factors, interleukins, interferons, and tumor necrosis factors) (Takx-Kohlen, 1992; Molloy et al., 1993). Cytokines are soluble, low molecular weight polypeptides and glycopepetides produced by a broad range of cell types that have suppressive or enhancing effects on cellular proliferation, differentiation, activation, and motility. For the most part, they are not constitutively secreted, but are produced in response to stimulation by infectious agents or their derived products (e.g., endotoxin), inflammatory mediators, mechanical injuries, and cytokines themselves (Kogut, 2000).

Interleukin-1 (IL-1), tumor necrosis factor-$\alpha$ (TNF-$\alpha$), and interferon (IFN) are three cytokines that participate in the immune response. IL-1 is involved in the host's response to antigenic challenge and tissue injury, and has been shown to increase the resistance of mice to pathogenic organisms such as *Listeria, Escherichia coli*, and *Candida albicans*

(Czuprynski and Brown, 1987; Cross et al., 1989; Pecyk et al., 1989). TNF-α and δ-IFN increased the resistance of mice to *Salmonella typhimurium* (Morrissey and Charrier, 1994). Human δ-IFNs have potent antiviral and antiproliferative activities, and are utilized as anticancer and antiviral therapeutic agents (Chang et al., 1999).

Three families of low molecular weight peptides that have immune regulatory properties are the tachykinins, the thymic hormones, and cationic peptides. The tachykinins are a family of closely related short neuropeptides that were initially identified by their activities as neurotransmitters. Tachykinins are now known to mediate such diverse activities as the proliferation of T-cells, release of TFN-γ, TNF-α, IL-1 and IL-6, and enhanced secretion of immunoglobulins (Maggio, 1990; Eglezos et al., 1991).

The thymic hormones are a family of proteins and peptides whose exact biological role is unknown. They are known to participate in the regulation and differentiation of thymus-derived lymphocytes and have been shown to act like cytokines. Some thymic hormones have been shown to reconstitute defective cell-mediated immunity in patients with various neoplastic diseases and secondary immune deficiencies as a result of chemo- and/or radiotherapy (thymic humoral factor) as well as enhance the production of IL-1, IL-2, IFN-γ and TNF-α (thymosin fraction 5) (Cohen et al., 1979; Dardenne and Savino, 1990).

Some cationic peptides have been observed to initiate an immunostimulant response. A decameric peptide was shown to impede the growth and spreading of established tumors (Folkman, 1999). Other peptides promote antibacterial, antifungal, antiviral, and even wound healing properties (Sanglier et al., 1993; Mizuno et al., 1995; Hancock, 1999). It is believed that these "defense" peptides are more general in their actions than antibodies, and as such, have a broader range of activity (Hancock, 1999).

SUMMARY OF THE INVENTION

The present invention overcomes the problems and disadvantages associated with current strategies and designs and provides isolated peptides for the treatment of diseases and disorders.

One embodiment of the invention is directed to isolated peptides comprising the sequence of SEQ ID NO 1, SEQ ID NO 2, SEQ ID NO 3, or SEQ ID NO 5. These peptides may contain a plurality of fatty acids groups coupled to one or more amino acids of said sequence.

Another embodiment of the invention is directed to methods for the isolation of peptides of the invention. Isolation is preferably by ultracentrifugation or dialysis. Alternatively, once their structure and sequence are known, peptides may be chemically synthesized.

Another embodiment of the invention is directed to a pharmaceutical composition comprising peptides of the invention.

Another embodiment of the invention is directed to methods for the treatment or prevention of diseases and disorders comprising administering isolated peptides of the invention to a patient.

Another embodiment of the invention is directed to antibodies or antibody fragments that are specifically reactive against peptides of the invention.

Another embodiment of the invention is directed to nucleic acid sequences, and sequences that hybridize thereto, that encode the peptides of the invention.

Advantages of the invention are set forth, in part, in the description which follows and, in part, will be obvious from this description and may be learned from the practice of this invention.

DESCRIPTION OF THE INVENTION

Figure 1:
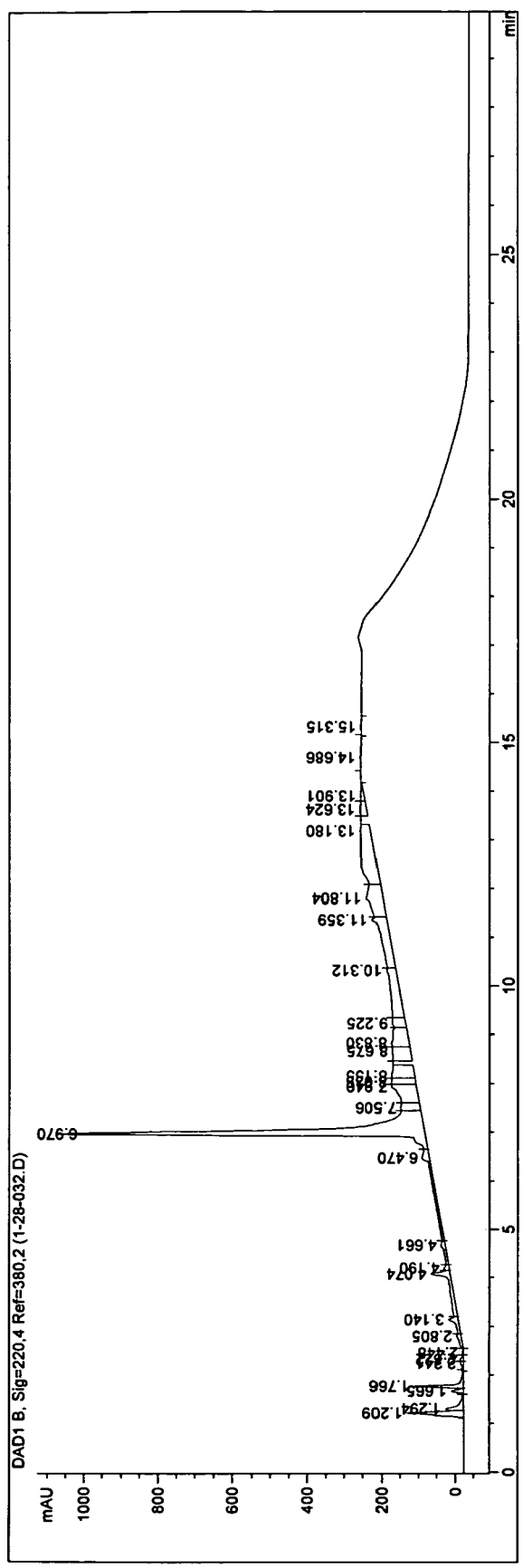
FIG. 1. HPLC analysis of serum fraction containing ICPF. Twenty µl of the serum fraction (5 mg/ml) was applied to a C-8 HPLC column (Eclipse XD8-C8, 4×150 mm) equilibrated in 0.1% aqueous TFA at a flow rate of 1 ml min$^{-1}$. A linear, binary gradient was established over 20 minutes to a final effluent containing 80% acetonitrile in 0.1% aqueous TFA. The effluent was monitored at 220 nm and 280 nm with a Hewlett Packard diode array detector (reference wavelength at 380 nm).

Current immuno-therapeutic agents provide a general stimulation to the patient's immune system which can be generally beneficial (Tizard, 1996) and of obvious benefit. Although these cytokinal factors such as the interferons often provide dramatic therapeutic results, they also require therapeutic dosages at concentrations that produce toxic side effects that are sometimes fatal and are not tolerated by many patients. As such these agents are not good candidates for wide spread, general use (Kruth, 1998).

In spite of the potential toxicities that can and do arise from therapeutic use of both generalized and specific immunostimulants, the potential benefits for stimulating the immune response are obvious and extensive. Therapeutic agents such as interferon are mainstream medical modalities in spite of their limitations. Adding to the arsenal of therapeutic agents, particularly one that may prove useful against neoplastic diseases as well as bacterial and viral pathogens, is very desirable. A simple and elegant means to accomplish this is to increase the assertiveness of the immune system in a more specific and selective manner. Use of selective immune regulating molecules would induce a specific and desirable reaction of the immune system that in turn would rapidly precipitate an enhanced therapeutic response while minimizing the untoward side effects and toxicities that are often observed from use of the less selective immunoregulators currently available. Initiation of such a specific immune response can be utilized to either act alone or in conjunction with conventional treatments and directed towards various etiological agents or disease states. Such an advancement in the therapeutic paradigm would have immediate and immense clinical impact. Further, an immuno-therapeutic agent of this nature would have obvious commercial value in the pharmaceutical market.

The present invention, which overcomes the problems and limitations encountered with current immuno-therapeutic strategies employing existing immunoregulators, is directed to ICPF that act in a well-described manner and in a dose dependent fashion. ICPF demonstrates a surprisingly low toxicity and low incidence of untoward reactions and side effects after administration of a dose several times the therapeutic dosage. Moreover, because the present invention describes a pharmaceutical grade chemical substance, the product can be manufactured with consistency, and the manufactured product can be free from contaminants, toxins, pyrogens and the like, and can have a verifiable quantity of active ingredient in each dose from lot-to-lot. Finally, the present invention discloses methods for the treatment of a surprisingly wide variety of human and animal diseases with bacterial, viral, and neoplastic etiologies, as well as methods for the prevention of human and animal infectious diseases.

Animal host models continue to serve to define general paradigms of cell-mediated immunity. Seminal studies of Listeria monocytogenes infection demonstrated the importance of activated macrophages in antibacterial defense, the role of lymphocytes for the development of specific resistance, and elucidated the interaction between the specific (lymphocyte) and nonspecific (macrophage) elements of the immune system (Mackaness, 1969; Shen et al., 1998). The advantages of and requisite need for reliable host models are clear and we further exploit this methodology to establish the efficacy and safety of the present invention.

One embodiment of the invention is directed to isolated peptides having an amino terminus and a carboxy terminus comprising the sequence of SEQ ID NO 3. These peptides may further comprises an arginine at the amino terminus and a phenylalanine at the carboxy terminus, and a plurality of fatty acids. The fatty acids may include at least one unsaturated fatty acid and, preferably, the fatty acids of said plurality are selected from the group consisting of stearic acid, arachidic acid, arachadonic acid, and combinations thereof. Preferably the isolated peptide is a nonapeptide. The isolated peptide may also comprise the sequence of SEQ ID NO 2, wherein $X_1$ and $X_2$ are derivatized or non-derivitized amino acids. Preferably $X_1$ comprises phenylalanine and $X_2$ comprises serine, which may be a serine-O-fatty acid ester.

Another embodiment of the invention comprises isolated peptides which comprises the sequence of SEQ ID NO 5. Most preferably, the peptide comprises the sequence of SEQ ID NO 1 wherein $R_1$, $R_2$ and $R_3$ represent fatty acid groups selected from the group consisting of stearic acid, arachidic acid, and arachadonic acid.

Another embodiment of the invention comprises methods for isolation of a peptide of the invention. Methods comprise dialyzing serum obtained from a mammal with a 1-20 kD or preferably a 6-10 kD cut-off dialysis membrane to produce a dialysate; and separating from said dialysate a fraction that elutes between 30 kD and 60 kD, and preferably between 40 kD and 50 kD. Alternatively, another method of isolating peptides of the invention comprises passing serum obtained from a mammal through a 70 kD to 100 kD cut-off ultrafiltration membrane to produce a filtrate, passing said filtrate through a 10 kD cut-off ultrafiltration membrane to produce a retentate, and isolating a fraction from said second retentate that has a median molecular weight of between 40 kD and 50 kD, and preferably between 42 kD and 48 kD. Preferably the mammal for such methods is a horse, a goat or a human. Alternatively still, once the amino acid sequence and chemical structure of the peptides of the invention are known and characterized, one of ordinary skill may chemically create the peptides of the invention using known recombinant techniques and/or chemical reactions.

Another embodiment of the invention comprises peptides of the invention capable of being isolated by one or more of the various methods of the invention.

Another embodiment of the invention comprises methods for the treatment or prevention of a mammalian disease or disorder in a patient comprising administering to said patient an effective amount of the isolated peptides of the invention. Preferably the mammalian disease or disorder is a bacterial, viral or parasitic infection, a cancer or other neoplasia, or a combination thereof. In such methods, the patient is preferably a mammal such as a human. The effective amount of the isolated peptides is that amount sufficient to produce an effective serum concentration for treating or preventing the specific disease or disorder. That amount can be empirically determined by those of ordinary skill in the art, and is expected to be between than 0.001 μg/ml and 100 μg/ml, preferably between 0.1 μg/ml and 50 μg/ml, more preferably between 1 μg/ml and 10 μg/ml.

Another embodiment of the invention comprises pharmaceutical compositions comprising isolated peptides of the invention combined with a pharmaceutically acceptable carrier. The pharmaceutical carrier may comprise water, an oil, an alcohol, glycerol, or a combination thereof. Preferably the pharmaceutical composition does not contain sufficient endotoxin to promote a pyrogenic response.

Another embodiment of the invention comprises an isolated antibody or antibody fragment that is specifically reactive against peptides of the invention.

Another embodiment of the invention comprises an isolated nucleic acid that encodes the sequence of peptides of the invention. Alternatively, nucleic acids may hybridizes in whole or in part to nucleic acid that encode such peptides.

Isolation and Chemical Characterization of ICPF

The following represents preferred methods for the isolation of ICPF of the invention. It is recognized by those of ordinary skill in the art that various modifications and other methods can also be used, as well as chemical and recombinant production of the ICPF of the invention.

Serum Preparation, Chromatographic Purification, and Spectral Characterization

ICPF was routinely isolated in gram-scale quantities from caprine serum by dialysis against distilled water (500 ml of serum and 3 L of distilled water) through a 6-8 kDa MWCO dialysis membrane (SpectraPor, Spectrum Laboratories, Inc., Laguna Hills, Calif.) for 10 hours and concentrated by lyophilization of the dialysate. This process yields between 4 and 4.5 grams of solid matter containing approximately 30% protein as determined by Kjeldahl analysis. This material is stored at −70° C. prior to use. This procedure provided sufficient material to conduct biological activity studies and initiate the chemical characterization of bioactive components.

Crude ICPF serum dialysate was reconstituted in distilled water at a concentration of 5 mg/ml (~1.5 mg protein/ml) and determined to be biologically active using the murine *Salmonella* challenge assay. Reverse phase chromatography revealed 5 major components in the serum dialysate (FIG. 1). LC/MS analysis characterized the first three components eluting between 1 min and 3 min as oligosaccharides and low molecular weight peptides (~1,000 amu). The minor component eluting around 4 min was characterized as a lipopeptide (<4,000 amu) and the major component eluting around 7 min was characterized as a lipopeptide (<4,000 amu). The quantitative analysis based upon the total mass abundance indicated that the component eluting around 7 min comprised >95% of the total protein matter in the mixture and was therefore the likely active ingredient.

The initial mass spectrometry (LC/MS) revealed several high mass fragments (1808.26, 1769.47, 1747.40, 1633.55, 1254.40, and 628.03 amu). No clearly recognizable parent ion was detected in the LC/MS experiments. The major component was isolated by preparative HPLC and purified ICPF was analyzed by MALDI-MS. The major positive ion fragments observed included 1798.8, 1713.9, 1696.4, 1599.0, 1322.7, and 683.4 amu. However, no clearly distinguishable parent ion was noted.

Figure 2:
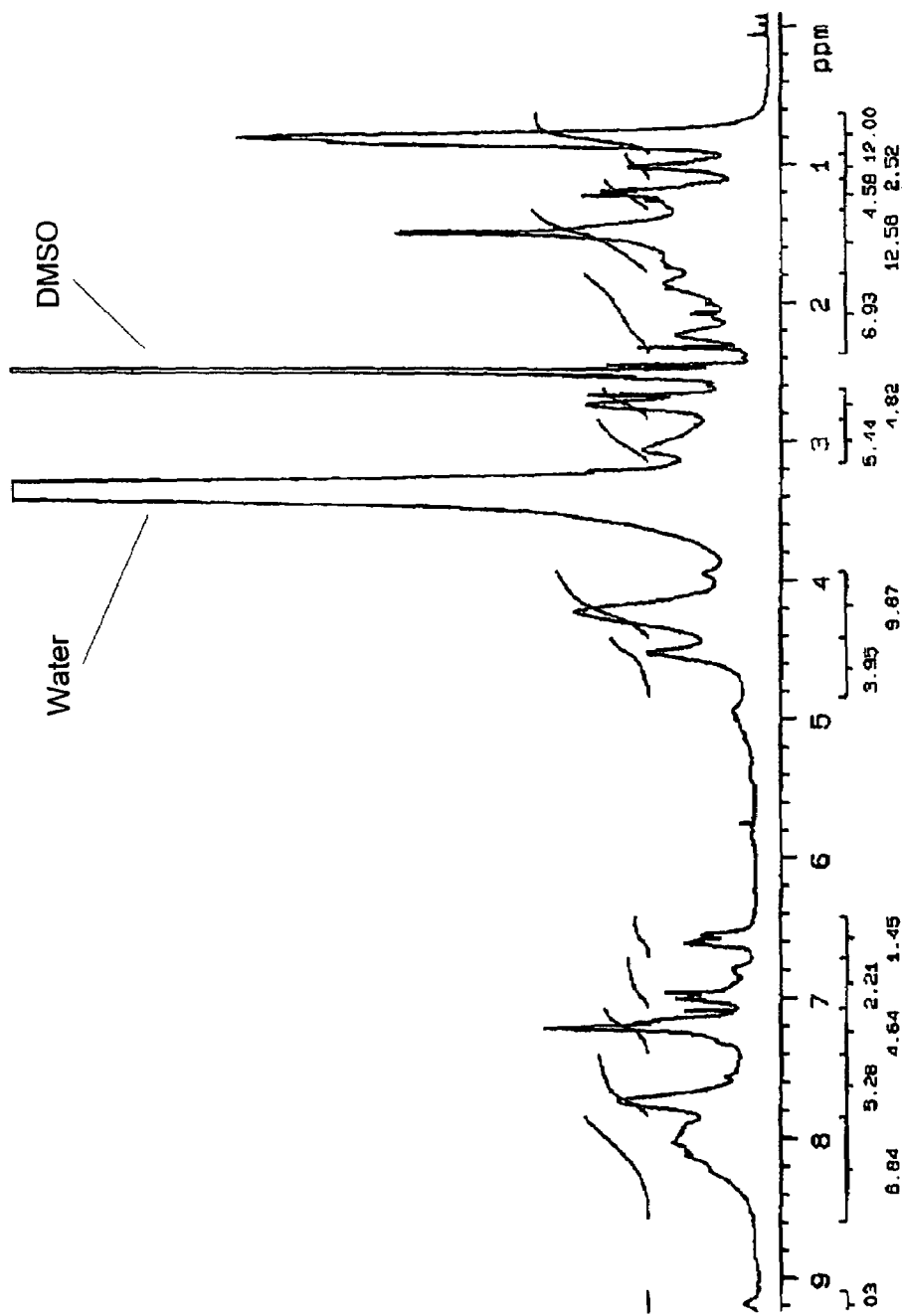
FIG. 2. $^1$H nuclear magnetic resonance spectrum of purified ICPF. Approximately 10 mg of purified ICPF was dissolved in d6-DMSO and the spectrum acquired in a NITY Plus-400 nuclear magnetic resonance spectrometer ($^1$H at 399.95 MHz). The radio frequency band width was 6000 Hz with a pulse angle of 45 degrees, a relaxation time of 1.0 seconds and an acquisition time of 2.601 seconds/scan. The total analysis time was 11 hours, 43 minutes, and 22 seconds.

Approximately 10 mg of purified ICPF was analyzed by 400 MHz $^1$H-nmr with d6-DMSO as the solvent (FIG. 2). Several key structural features are revealed. Beginning with the low field region of the spectrum an acidic proton absorbance is observed at 9.2 ppm and is consistent with the phenolic hydrogen of tyrosine. The aromatic region reveals a large multiplet centered around 8.0 ppm and another split multiplet (J=200 Hz) that may indicate the presence of phenylalanine and tyrosine respectively. Vinylic hydrogens are observed in the region of 6.6-7.0 ppm that could be accounted for by an unsaturated fatty acid. The possibility of a fatty acid is further suggested by the large number of methylene hydrogen signals centered around 0.8 ppm and the methylenes α to carbonyls or vinylic carbons in the region around 1.5 ppm. Extensive conjugation of the peptide with fatty acids could also account for the broadening of the aromatic signals that would arise from anisotropic shielding effects of the methylene protons. The broad signals in the 4.0-5.0 ppm region are consistent with the absorbance of the α-methylene hydrogens of a peptide bond.

Peptide Sequencing by Edman Degradation

Approximately 20 mg of purified ICPF was collected by preparative scale HPLC and the purity was determined to be >96% (96.38%). The amino acid sequence was determined by the Edman degradation method using an auto-sequencer (Procise, Applied Biosystems, Inc.). These results indicated a primary sequence of Arg-$X_1$-Val-Ser-Leu-Ser-Tyr-Arg-$X_2$ (SEQ ID NO 2) wherein $X_1$ and $X_2$ represent amino acids that could not be immediately identified that may be the same or different. The identifiable core sequence comprises Val-Ser-Leu-Ser-Tyr-Arg (SEQ ID NO 3).

Acid Hydrolysis

To identify the unknown amino acids and the conjugates, another 20 mg of ICPF was purified by preparative HPLC and approximately 10 mg was subjected to standard acid hydrolysis (6N HCL for 5 hours) followed by HPLC/MS analysis and MALDI-MS analysis of the hydrolysate.

The MALDI-MS revealed several lower mass positive ion fragments, most notably, fragments corresponding to phenylalanine at 147.3 amu and 165.2 amu. The presence of these two ion fragments established the presence of phenylalanine as one of the two amino acids not identified by the Edman degradation. Other major positive ion fragments observed included 173.1 (Arginine), 191.2 (Arginine+water of hydration), 295.2, and 336.23 amu. The major negative ions observed in the MALDI-MS included 778.9, 189.0, 145.1, and 94.1 amu. Amino acid analysis of this fraction differed from that suggested by the Edman degradation only in the presence of phenylalanine. Thus, the remaining amino acid that was not identified by the Edman degradation may be one of the amino acids already identified in the peptide sequence, possibly serine.

Figure 3:
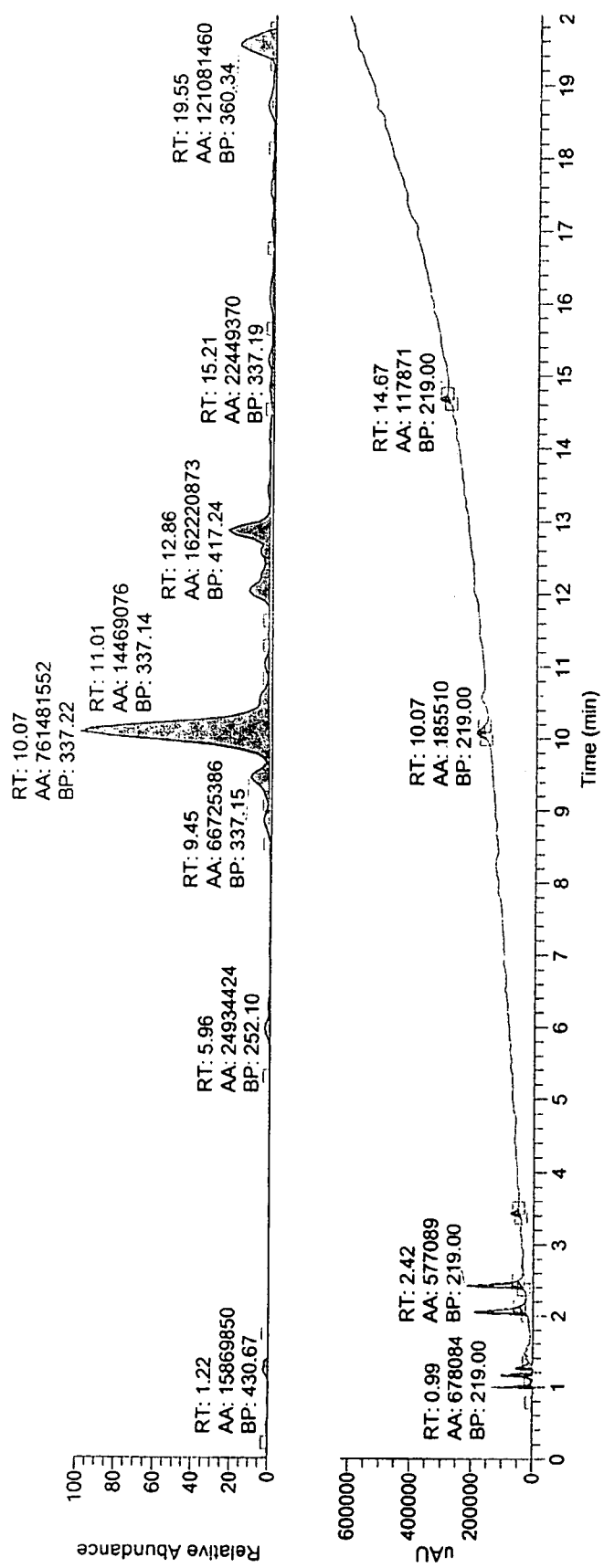
FIG. 3. Total ion abundance chromatogram of the ICPF acid hydrolysate. HPLC\MS analysis of the acid hydrolysate was performed with a Finnegan Surveyor HPLC interfaced to a Finnegan LCQ Classic Mass Spectrometer using electrospray ionization at 5 Kv. Chromatographic separation of the hydrolysate components was achieved using a C-18 reverse phase column (4.6 mm×100 mm, 3 µm particle diameter with 100 angstrom pore size). The mobile phase was a linear gradient formed over 20 minutes from 5% acetonitrile in 0.1% aqueous trifluoroacetic acid to 100% acetonitrile with 0.1% trifluoroacetic acid at a flow rate of 1 ml min$^{-1}$.

Reverse phase HPLC/MS analysis of the acid hydrolysate contained one major component eluting at 10.07 minutes and several minor components. The total abundance ion chromatogram is depicted in FIG. 3. The mass spectral analysis of the peak eluting at 10.07 minutes had major fragments ions at 337.22, 422.01, and 507.04 amu the latter of which appeared to be consistent with a parent ion.

Alkaline Hydrolysis

Approximately 10 mg of ICPF was hydrolyzed under alkaline conditions (1N NaOH for 10 hours) followed by HPLC/MS of the hydrolysate to identify the suspected fatty acids. The conditions for alkaline hydrolysis and HPLC/MS analysis had been previously optimized from the hydrolysis of a known lipopeptide (Gly-Ser-Ser(Octanoyl)-Phe-Leu-Ser-Glu) (SEQ ID NO 4).

Figure 4:
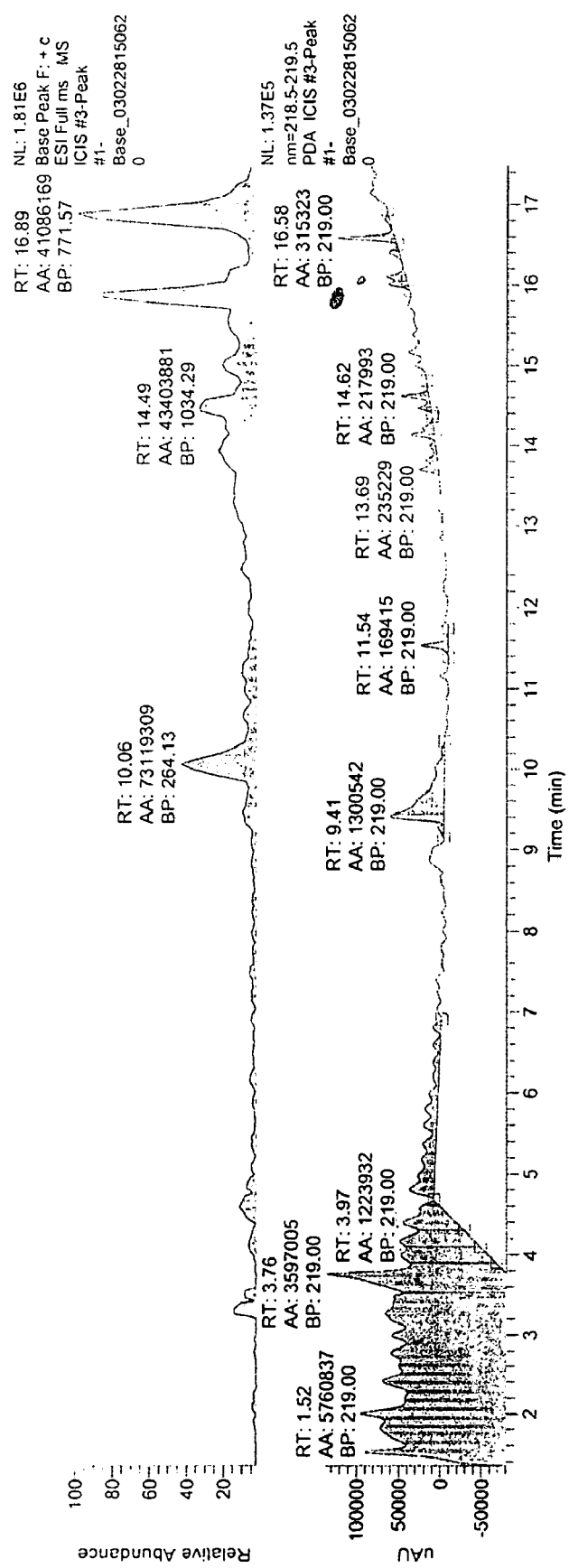
FIG. 4. Total ion abundance chromatogram of the ICPF alkaline hydrolysate HPLC\MS analysis of the alkaline hydrolysate was performed using a Finnegan Surveyor HPLC interfaced to a Finnegan LCQ Classic Mass Spectrometer using electrospray ionization at 5 Kv. Chromatographic separation of the hydrolysate components was achieved using a C-18 reverse phase column (4.6 mm×100 mm, 3 µm particle diameter with 100 angstrom pore size). The mobile phase was a linear gradient formed over 20 minutes from 5% acetonitrile in 0.1% aqueous trifluoroacetic acid to 100% acetonitrile with 0.1% trifluoroacetic acid at a flow rate of 1 ml min$^{-1}$.

Three major peaks were observed in the HPLC chromatogram with retention times of 10.06, 15.97, and 16.89 minutes as shown in FIG. 4. MALDI-MS of the hydrolysate revealed positive ion fragments with masses at 862.66, 673.54, 657.54, 446.59, 267.44, 251.44, 235.44, 213.4, and 105.24 amu. The primary negative ion fragments noted in the MALDI-MS included 400.29, 325.25, 189.21, and 145.17 amu.

Upon closer examination of the peak eluting at 10.06 minutes in the HPLC chromatogram (FIG. 4), it was noted that there are actually two co-eluting components. MALDI-MS of the first peak detected three major high mass fragment ions at 1783.96, 1562.75, and 1540.73 amu. The second eluting component had two major high mass fragment ions at 1801.94 and 1158.94 amu.

Molecular Modeling Studies

Lowest energy conformation was determined by successive iterations of calculating the lowest energy (heat of formation) using MOPAC with MNDO theory applied followed by lowest steric energy using MM2 (Chem 3D 7.0, Cambridge Software, Cambridge, Mass.). Successive iterations were repeated until the heat of formation did not change between iterations. Upon obtaining the lowest energy conformation the theoretical NMR chemical shifts were calculated for comparison to the experimentally measured chemical shifts.

Chemical Structure

The foregoing chemical and spectral evidences present a compelling argument for a chemical structure for ICPF that contains the following elements (i) a nonapeptide in which the amine terminal residue is arginine and the carboxylate terminal residue is phenylalanine, (ii) a serine-o-fatty acid ester is the second amino acid in the sequence of the nonapeptide, and (iii) up to a total of 3 long chain fatty acids, one of which is an unsaturated fatty acid, are present in ICPF. The fatty acids contained in ICPF include stearic acid, arachidic acid, and arachadonic acid. Moreover, one embodiment of ICPF may be characterized as a 1-peptidyl-(2,3)-diacyl-O-glycerol lipopeptide comprising the nonapeptide sequence Arg-Ser-Val-Ser-Leu-Ser-Tyr-Arg-Phe- (SEQ ID NO 5). The entire chemical structure presented in FIG. 5 (SEQ ID NO 1) wherein $R_1$, $R_2$ and $R_3$ represent fatty acids) is consistent with the chemical and spectral evidence as presented herein and represents a preferred embodiment of ICPF of the invention.

Beginning with the acid hydrolysis of ICPF, the fragment ion at 295.20 in the MALDI-MS is consistent with arachidic acid. The fragment at 337.2 amu in the HPLC/MS analysis of the major component eluting at 10.07 minutes is consistent with [arachidacyl-O—$CH_2$—CH+] which could have arisen from an arachidacylglycerol ester. The corresponding ion fragment at 336.23 amu in the MALDI-MS would then be explained as [arachidacyl-O—$C^+$=$CH_2$]. The HPLC/MS fragment ion at 422.01 is consistent with the loss of a neutral $C_{18}H_{34}$ fragment from [arachidonacyl-O—$CH_2$—CH—O (arachidacyl)-$CH_2$OH]. The highest mass fragment observed in the HPLC/MS spectrum was 507.04 and is consistent with the [arachidonacyl-O—CH—$C^+$H—CH2—O-Phenylalanyl.] radical ion.

Turning now to the alkaline hydrolysis experiments, the MALDI-MS confirmed the presence of stearic acid from the positive ion fragment ion at 267.44 amu that conforms to the loss of $^-$OH from the stearic acid. The [arachidonacyl-O—$CH_2$—CH—O(arachidacyl)-$CH_2$OH] fragment suggested in the HPLC/MS of the acid hydrolysate was confirmed by the ion fragment at 673.4 [arachidonacyl-O—$CH_2$—CH—O (arachidacyl)-$CH_2OH_2^+$] in the MALDI-MS of the alkaline hydrolysate.

Figure 5:
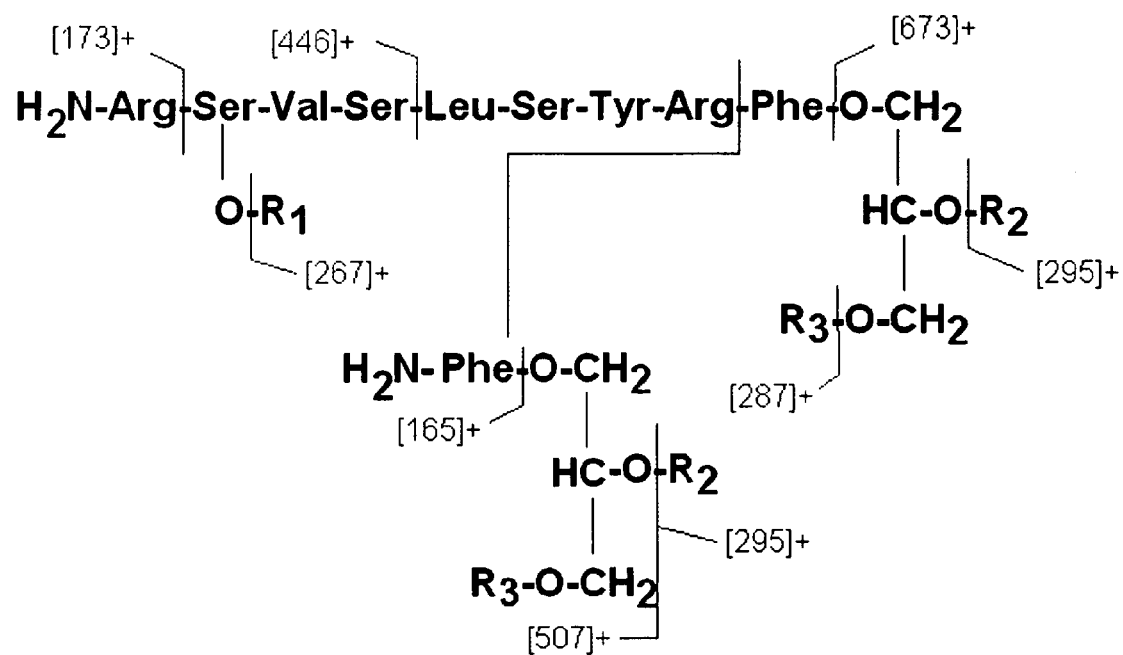
FIG. 5. Chemical structure of ICPF where R1 is stearate, R2 is arachidate, and R3 is arachidonate (SEQ ID NO 1). Key ion fragments in the MALDI-MS and electrospray MS are indicated. The major products from both acid and alkaline hydrolysis are depicted along with the major ion fragments observed in the mass spectral analyses where fragment ions were observed after alkaline hydrolysis and after acid hydrolysis.

The remaining structural features suggested in the model depicted in FIG. 5 are revealed through the chemical hydrolysis and the resulting mass spectral fragmentation patterns also depicted in FIG. 5 and these are clearly discernable by those practiced in the art.

Antibiotic and Virucidal Properties

The following represent preferred advantages of ICPF of the invention. It is understood by those of ordinary skill in the art from the complete disclosure and the exemplars herein that ICPF of the invention can be used broadly to treat or prevent a variety of diseases and disorders including viral, bacterial and parasitic infections.

Antimicrobial Sensitivity

ICPF was assessed for antimicrobial activity against a variety of both gram positive and gram negative bacteria by performing disk agar diffusion assays. Antibiotic minimum inhibitory concentrations (MICs) were determined in Mueller-Hinton broth using the broth dilution method. ICPF failed to inhibit the growth of all test bacteria. The minimum inhibitory concentration (MIC) for a cationic peptide is usually in the range of 1 to 8 μg/mL (Hancock, 1997). There was no zone of growth inhibition when ICPF was tested at 20 mg/mL, over 2,500 times the upper MIC range recognized for cationic peptides.

Virucidal Sensitivity

The virucidal and antiviral interactions between ICPF and Canine Parvovirus (CPV) were assessed by ViroMed Biosafety Laboratories (St. Paul, Minn.). To accurately assess ICPF's virucidal activity to CPV it was necessary to first establish if the viability of the host cell line (canine fibroblast A-72 endothelial cells) was impaired by the presence of ICPF. Cell proliferation was not affected adversely when exposed to ICPF at concentrations from 0.001-100 μg/ml ICPF. ICPF was not virucidal to CPV as infectivity and proliferation were not affected by prior exposure to ICPF. The in vivo antiviral activity of ICPF was also assessed in this cell line. There was no evidence in these experiments that ICPF promoted antiviral activity within the host cell.

TABLE 1

| Organism | Zone of inhibition ICPF | |
|---|---|---|
| | 4 h | 24 h |
| Gram-negative bacteria | | |
| Pseudomonas aeruginosa ATCC 27853 | 0 | 0 |
| Pseudomonas aeruginosa PAO1 | 0 | 0 |
| Escherichia coli ATCC 25922 | 0 | 0 |
| Enterobacter aerogenes | 0 | 0 |
| Enterobacter cloacae | 0 | 0 |
| Salmonella typhimurium | 0 | 0 |
| Pasteurella multocida ATCC 11039 | IG | 0 |
| Pasteurella multocida P-1581 | IG | 0 |
| Gram-positive bacteria | | |
| Staphylococcus aureus | 0 | 0 |
| Staphylococcus aureus T-5706 | 0 | 0 |
| Bacillus subtilis | IG | 0 |

Table 1: Mueller-Hinton agar plates were streak inoculated with each of the assay organisms. Sterile filter paper disks impregnated with ICPF were aseptically applied to the seeded plate surfaces. The plates were incubated for 24 h at 37° C., during which time inhibition of growth in areas surrounding the disks were visually assessed at 4 and 24 h. (IG = insufficient growth).

Mode of Action

The following represents preferred modes of action of ICPF of the invention. It is recognized by those of ordinary skill in the art that from the complete disclosure and from the exemplars herein that additional modes of action may be associated with the ICPF of the invention.

Macrophage Activation

J774A.1 macrophages (ATCC TIB67, 5×10$^4$ viable cells/well) were cultured in Dulbecco's Modified Eagle Medium (DMEM, high glucose)+10% FBS+100 U/ml penicillin+100 μg/ml streptomycin for 24 hr prior to treatment addition. NO production was determined colorimetrically using the Greiss reagent 24 hr after experimental treatments. Means of experimental groups were considered significantly different if $p \leq 0.05$. Statistical significance was analyzed by comparison of mean values using the Student's t test (unpaired, two-tailed).

ICPF doses up to 1000 μg/ml, with or without IFN-γ, did not induce NO synthesis. Purified peptide from ICPF (0.1-100 μg/ml) also failed to induce NO in the absence or presence of IFN-γ.

Neither ICPF (100 μg/ml) nor ICPF-peptide (10 μg/ml) altered the dose of LPS required to induce NO in IFN-γstimulated J774A.1 macrophages. Combinations of ICPF (100 μg/ml) or ICPF-peptide (10 μg/ml) with varying doses of LPS (0-10 μg/ml in the absence of IFN-γ) were also unable to induce NO.

Neither ICPF (100 μg/ml) nor ICPF-peptide (10 μg/ml) altered the dose of IFN-γ required to induce NO in LPS-stimulated J774A.1 macrophages. ICPF-peptide (0.1-100 μg/ml) also did not modulate the amount of NO induced by the minimal stimulatory dose of LPS (10 ng/ml)+IFN-γ (1-5 U/ml).

Natural Killer Cell Activation

To determine if ICPF was directly activating NK cells, splenocytes derived from mice treated with saline or ICPF were assayed for NK activity with the standard chromium-release assay. The data show that ICPF does not directly activate NK cells in naive mice at E:T ratios of 200:1, 100:1, and 50:1. The results are depicted in Table 2. The mice used in these experiments, however, contained viable NK cells as shown with poly I:C induced activation of NK cells.

TABLE 2

| | Percent $^{51}$Cr released at E:T ratios | | |
|---|---|---|---|
| | 200:1 | 100:1 | 50:1 |
| Saline | 4.0 ± 0.9$^a$ | 3.0 ± 0.5$^a$ | 1.4 ± 0.7$^a$ |
| ICPF | 4.8 ± 0.9$^a$ | 7.3 ± 1.1$^a$ | 3.9 ± 0.8$^a$ |
| Poly I:C | 35.3 ± 1.6$^b$ | 31.5 ± 1.1$^b$ | 19.1 ± 1.0$^b$ |

$^{a-b}$Means in a column with no common superscript differ significantly (P < 0.05).
Table 2. Mice were given 0.25 ml i.p. of either one of three treatments: 5 mg ICPF, physiological saline, or 20 μg Poly I:C. Spleens were harvested the following day and assessed for NK cell activity with the standard chromium-release assay. Data are presented as the mean (n = 3) with its associated standard experimental error.

Figure 6:
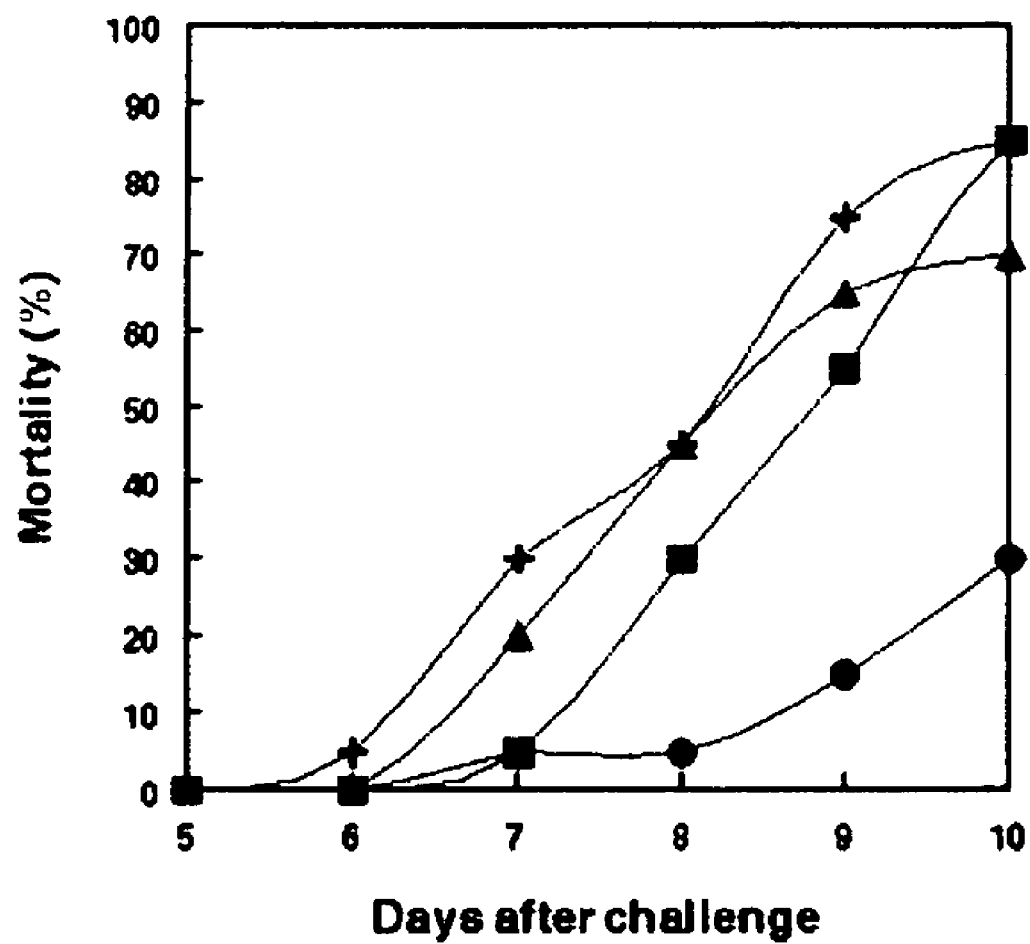
FIG. 6. NK cell depletion model. All mice were administered 0.1 ml (~5~10$^3$ cfu {colony forming units}) of *S. typhimurium* i.p. on day 0. Mice were supplemented on day −1 with either physiological saline (positive control mice: +), 100 µl anti-asialo GM1 (NK depleted mice: ▲), 5 mg ICPF (ICPF treated mice: ●), or anti-asialo GM1 and ICPF (■). Each data point represents the average daily mortality (n=5) with its associated standard experimental error per cage of 5 mice.

While there was no apparent direct activation of NK cells, it was important to establish if NK cells participated in ICPF-mediated events. To test this possibility, control or ICPF treated mice were depleted of NK cells by injection of anti-asialo GM-1 and then challenged with a lethal dose of S. typhimurium. By day 10, 85% of the control mice were dead, and there was no significant difference from either group of mice depleted of NK cells, including those that had also received ICPF. In contrast, however, only 30% of the NK cell intact, ICPF-treated mice died by day 10. These results are depicted in FIG. 6.

Acute Phase Protein Production

Figure 7:
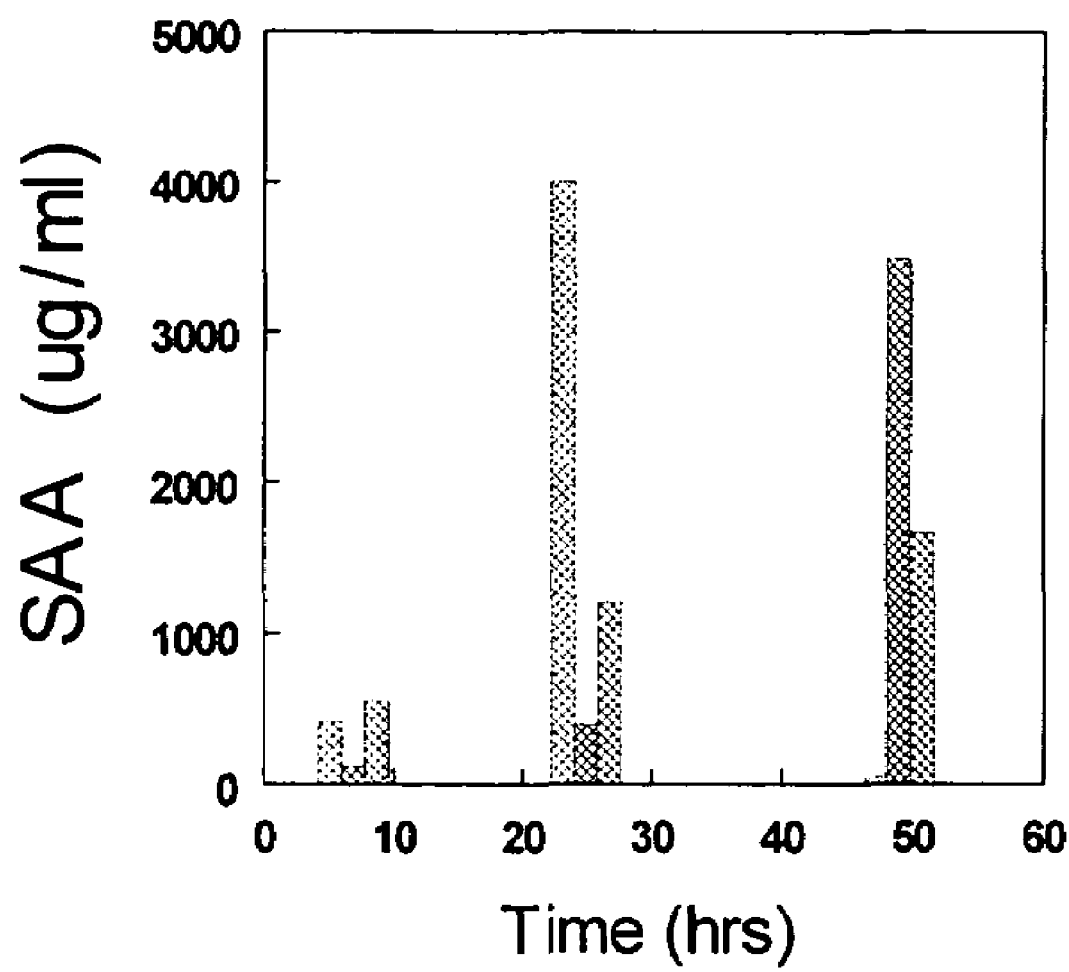
FIG. 7. Acute phase protein profile. Mice were assigned to one of four treatment groups: Control mice (not shown), salmonella-infected mice (left bar), ICPF-treated mice (middle bar), and Salmonella infected, ICPF treated mice (right bar). Mice were administered 0.1 ml (~5×10$^3$ cfu) of S. typhimurium or a placebo i.p. on day 0, while ICPF-treated mice received a 0.25 ml subcutaneous injection of ICPF (5 mg) on day −1. At time 0 (baseline), and 6, 24, and 48 hours after challenge five mice from each group were selected randomly and serum obtained by cardiac stick. Serum samples were frozen at −70° C. until they were analyzed for serum amyloid A (Tridelta Development Ltd., Greystones, Ireland).
Figure 8:
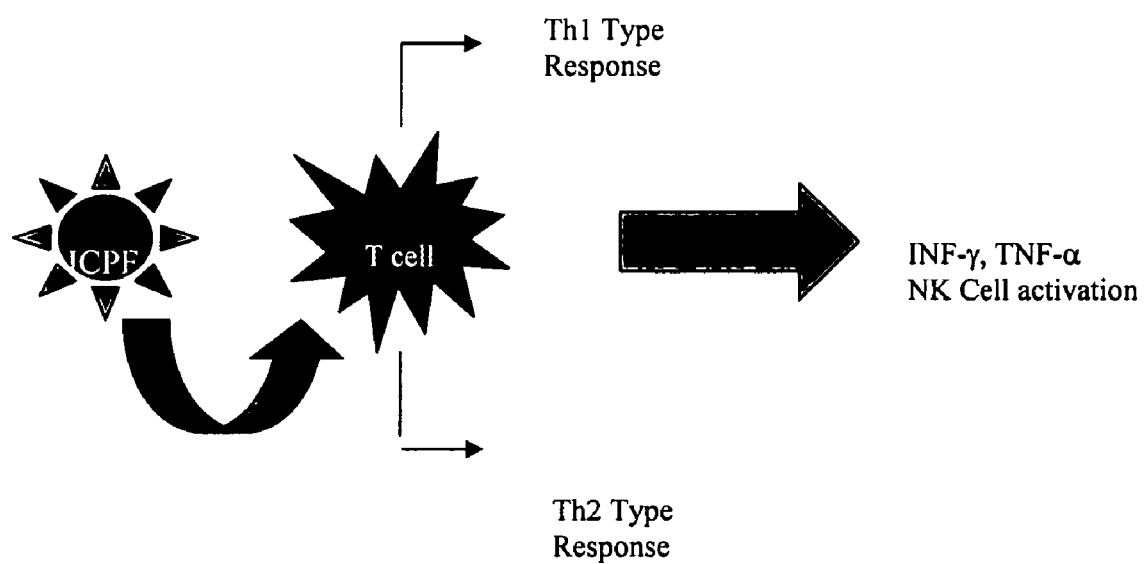
FIG. 8. ICPF binds to a specific receptor on a T lymphocyte (TCR) such as the γδ-T cell. Cytokines, IF-γ and TNF-α for instance, are produced that in the presence of other cofactors, like LPS for example, activate cytotoxic and phagocytic cells of the innate immune system (natural killer cells (NK cells), macrophage, etc.) and stimulate the production of the acute phase proteins in the liver.

Four treatment groups were established: negative control (mice which received neither a bacterial challenge nor ICPF), positive control (mice which received a bacterial challenge but no ICPF), ICPF treated mice (mice which received both a bacterial challenge and ICPF), and the treatment control (mice which received ICPF but no bacterial challenge). At time 0 (baseline), and 6, 24, and 48 hours after challenge five mice from each group were selected randomly and blood drawn from the inferior vena cava and centrifuged to obtain serum. Samples were frozen at −70° C. until they were analyzed for the acute phase proteins serum amyloid A (SAA) and haptoglobin (Tridelta Development Ltd., Greystones, Ireland). At 24 hours, the *Salmonella* group had significantly higher levels of haptoglobin and SAA. However, these levels dropped by 48 hours, while the levels increased in both ICPF treated groups. These results are depicted in FIG. 7.

The drop in acute phase proteins in *Salmonella* infected mice may be due to liver damage affecting their ability to release acute phase proteins, and therefore this could once again show that ICPF is effective in delaying the effects seen due to salmonellosis. However, since mice which only received ICPF also show significant increases 72 hours after injection (day −1 until 48 hours post-challenge), it may be that ICPF possesses an ability to increase the release of acute phase proteins. Acute phase proteins are released from the liver in response to the release of the proinflammatory cytokines (e.g., IL-1, IL-6, and TNF-$\alpha$) from various mediators, such as activated macrophages, monocytes, granulocytes, etc. (Dinarello, 1984; Beutler and Cerami, 1986; Heinrich et al., 1990; Waage et al., 1992). Therefore, ICPF's mode of action may involve an activation event upstream of cytokine release, thus initiating an inflammation cascade.

Antibody Production

Six New Zealand White female rabbits (two groups of 3 rabbits) received 0.25 ml of Freund's Complete Adjuvant with or without 5 mg of ICPF. Blood samples were drawn one day prior (day −1) to inoculation and on days 4, 7, 9, 11, 14, 16, 18, and 21. Serum from all bleeds was collected and analyzed for total and specific antibody production by ELISA. A comparison of the *M. tuberculosis* specific antibody titers in the ICPF treated and untreated rabbits indicated that ICPF increased the specific antibody production nominally 1,000-fold over the untreated control rabbits.

The immune response in mammals has been conceptually and functionally described as either an adaptive or an innate immune response. In this characterization the adaptive immune response provides long-term protection from re-infection through clonal expansion of specific memory cells and antibody production. The innate immune response, on the other hand, provides a 'first line of defense' against invading pathogens and is characterized by the activation of various cytotoxic and phagocytic cells. Animal models have shown that ICPF provides prophylactic protection from a massively lethal challenge with bacterial pathogens and even metastatic melanocytes. ICPF acts therapeutically against established infections of both bacterial and viral etiology. These observation suggests that ICPF 'primes' circulating or tissue resident immune cell(s) so that a more effective innate immune response can be mounted by the host when challenged with the pathogen and that in established infections ICPF may up-regulate the cytotoxic and phagocytic immune cells.

Circulating and tissue resident macrophages are one of the primary immune cells responsible for innate immunity. In vitro studies with isolated macrophage cell lines have provided evidence that ICPF does not directly stimulate macrophage. However, in vivo, the acute phase protein profile is significantly affected by ICPF. Since ICPF has a role in the release of acute phase proteins, and acute phase protein release is mediated by the release of cytokines, ICPF may also affect the release of cytokines from an upstream effector cell. Natural Killer (NK) cells, while not directly stimulated by ICPF, are a functional participant in the ICPF cascade.

T-cells are an important class of lymphocytes and have been classified by the differential expression of T cell receptors (TCR) as either αβ or γδ heterodimers. Research has previously focused on the αβsubset and has clearly established their role in the adaptive immune response through recognition of antigens via antigen presenting cells and TCR binding with the major histocompatability complex (MHC). This response is generally referred to as a Th2 type response.

The γδ-T cells have long been considered innate immune cells and until recently represent a less well studied cell lineage. In humans the γδ-T cell is less prevalent than its αβ cousin and constitutes only about 5% of the lymphocyte population. γδ T cells can undergo clonal expansion to constitute up to 97% of the total T cell population in a wide variety of infections (Poquet, 1998). The impact of γδ T cells on macrophage and NK cell activation has been reported in a murine model (Carding, 2002). Mice deficient in γδ T cells have also been shown to be less able to withstand bacterial infection and were characterized by disruption of macrophage homeostasis, reduced INF-γ production from NK cells, and increased bacterial growth (Ladel, 1996). The graphic depiction in FIG. 8 describes a mode of action of ICPF and is consistent with existing experimental evidence and the current knowledge of the mammalian immune response.

Methods of ICPF Production

The following represents preferred methods for the production of ICPF of the invention. It is recognized by those of ordinary skill in the art from the complete disclosure and the exemplars herein that various modifications of these methods as well as other methods can also be used to manufacture the ICPF of the invention.

To provide a marketable product, it is typically necessary to develop a process that can produce kilogram quantities of highly purified ICPF from serum on a continual and reliable basis. Dialysis of serum, although satisfactory for producing research quantities of ICPF, is not usually a scaleable process. Disclosed here is a process to produce a purified fraction of serum that contains predominantly ICPF using a scaleable ultrafiltration (UF) process.

Raw Serum Procurement

Sterile equine serum was procured from Equitech-Bio, Inc. (Kerrville, Tex.) and was shipped frozen to Stolle Milk Biologics, Inc. (Cincinnati, Ohio). The serum was collected from donor horses of USA origin that have been certified free of Equine Infectious Anemia and sterile filtered. Each serum lot shipped was certified sterile and free of *Mycoplasma* species. All production of serum was carried out in accordance with cGMP guidelines.

Ultrafiltration of Raw Serum

Two-stage ultrafiltration was performed on a temperature controlled 10-liter bench-top spiral-wound ultrafiltration membrane system pumped by a Tri-Clover rotary pump (model PR3-1M-UH6-SL-S). Temperature was maintained at 8° C.+/−2° by circulating the serum retentate through an in-line heat exchanger cooled by a cooling circulator. All metal components were stainless steel. Serum retentate was contained in a sanitized holding container.

Stage 1—Two liters of serum was thawed and diluted with 8 liters of cold (4° C.) freshly prepared pyrogen-free deionized water. The cold diluted serum was pumped through a 72 $ft^2$ 70-100 kDa cut-off spiral wound ultrafiltration membrane (Desal model EW1812C) at a pressure of 40 psig. The filtrate was collected at a flux rate of 150 ml per minute in a sanitized container maintained at 4° C. in an ice water bath. Filtration was continued until the retentate was reduced to 1000 ml.

Stage 2—The ultrafiltrate from stage 1 was pumped through a 72 ft$^2$ 10 kDa cut-off spiral wound ultrafiltration membrane (Desal model PW1812C) at a pressure of 40 psig. The stage 2 filtrate was collected at a flux rate of 40 ml per minute in a sanitized container. The retentate temperature was maintained at 10° C. +/−2°. Filtration was continued until the retentate was reduced to 1000 ml. The 10 Kda retentate was sterile filtered and frozen at −20° C.

Reversed Phase HPLC Analysis

Filtrate and retentate samples from both stage 1 and stage 2 were analyzed by reversed-phase HPLC on a Hewlett-Packard 1100 Series HPLC with a diode array detector on an SB-C$_{18}$ column (Zorbax) in an acetonitrile (ACN)-trifluoroacetic acid (TFA)-water mobile phase. Samples were eluted with a gradient of 5-100% ACN containing 0.1% TFA. The effluent was monitored at 220 and 280 nm.

For the isolation of ICPF and the subsequent size exclusion chromatography (SEC) analysis, 22.5 mg of caprine dialysate was dissolved in 0.1% TFA and chromatographed in 14 runs on a C-18 column and the effluent was collected in a fraction collector. Fractions containing the ICPF peak eluting at 9.815 min were pooled and dried under N2. An aliquot of the isolated ICPF was reserved and re-analyzed on C18 to confirm the presence of a single ICPF peak eluting at the appropriate retention time (9.8 min).

Size Exclusion Chromatography

ICPF prepared by ultrafiltration were analyzed by size exclusion chromatography (SEC) and compared to ICPF prepared by dialysis. Size exclusion analysis was accomplished using 7.8×30 mm, TSK G3000SWx1 (TosoHaas) size exclusion column packed with a 5 um particle with a 250 angstrom pore size. The column was calibrated using a standard mixture of molecular weight markers (BioRad) and the effluent was monitored at 220 and 280 nm. The ICPF fractions that were collected from preparative reversed phase chromatography were combined, dried under N$_2$, and dissolved in 0.2M sodium phosphate, 0.15M sodium chloride, pH 6.8 mobile phase.

Purification by Alcohol Extraction

ICPF prepared by both dialysis and ultrafiltration was extracted with either methanol or ethanol. The alcohol soluble material was analyzed by both reversed phase HPLC and size exclusion HPLC. The residue remaining after alcohol extraction was dissolved in 0.2M sodium phosphate, 0.15M sodium chloride, pH 6.8 and analyzed by both reversed phase HPLC and size exclusion HPLC.

UV Spectral Analysis

The total UV spectrum over the range of 190 nm-350 nm for ICPF prepared by both dialysis and ultrafiltration and analyzed by size exclusion HPLC was taken at selected time points during the elution profile to correspond to the different molecular weight fractions observed.

The standard method for preparation of research quantities of ICPF has been dialysis in a 10 kDa dialysis bag against deionized water followed by concentration of the dialysate. Chemical characterization of ICPF has clearly established the chemical structure and molecular weight of ~2,000 dalton. Surprisingly the ultrafiltration fraction that contained ICPF was not the expected 10 kDa filtrate, but the 10 kDa retentate. This result was observed from both caprine and equine derived serum.

Figure 9:
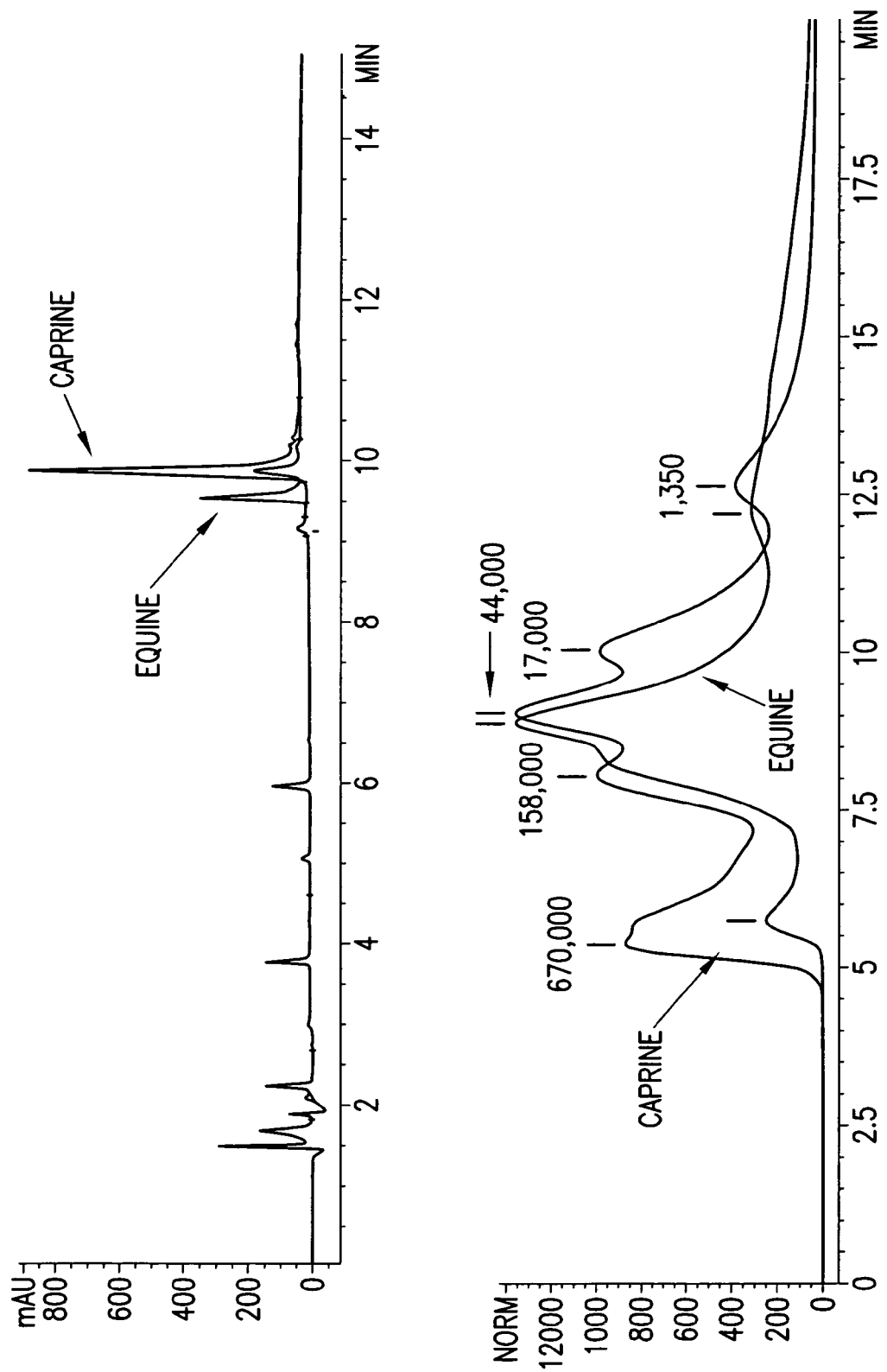
FIG. 9. An overlay comparison of the caprine derived ICPF prepared by dialysis and the equine derived ICPF prepared by dialysis using reversed phase HPLC and monitoring the column effluent at 220 nm (top). An overlay comparison of the caprine derived ICPF prepared by dialysis and the equine derived ICPF prepared by dialysis using size exclusion HPLC and monitoring the column effluent at 220 nm (bottom).

Reversed phase chromatographic comparisons of the caprine and equine derived ICPF show similar elution profiles during reversed phase HPLC and size exclusion HPLC (FIG. 9). The difference in the ICPF retention time in reversed phase HPLC may be attributable to differences in the type of lipids that are conjugated to the peptide backbone. Mortality abatement of ICPF in our murine *Salmonella* model has established the bio-equivalency of caprine and equine derived ICPF.

Previous chromatographic analysis has demonstrated that caprine ICPF dialysate gives rise to 22 observed components on C18 reversed phase HPLC. The major component at ~9.8 min, presumably ICPF, represents approximately 58% of the total observed peak area at 220 nm. Nine smaller peaks represent 36% of the total area and 12 minor components account for the remaining 6%. Under the conditions of HPLC-MS, the total ion chromatogram indicated that the ICPF peak accounted for ~90% of the total ion abundance and is probably a better indicator of the total abundance of ICPF on a mass basis.

Figure 10:
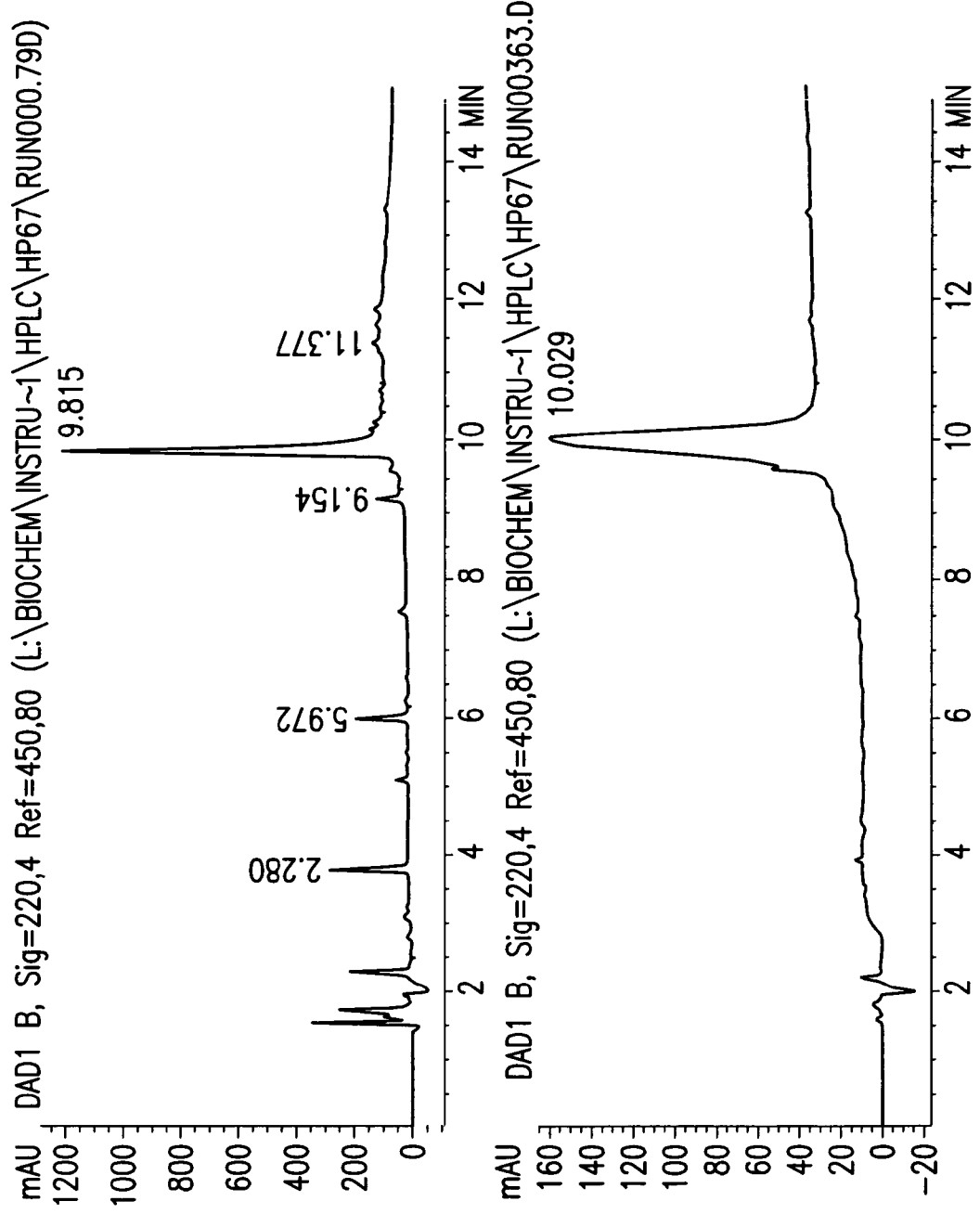
FIG. 10. A comparison of the reversed phase HPLC elution profile at 220 nm for ICPF before (top) and after (bottom) alcohol extraction. The ICPF sample was dissolved in the mobile phase for analysis prior to alcohol extraction. After alcohol extraction, the residue remaining was dissolved in 0.2M sodium phosphate, 0.15M sodium chloride, pH 6.8 prior to analysis.

Analysis of caprine dialysate by size exclusion HPLC revealed 6 major fractions eluting at molecular weights of 970,000, 512,000, 217,000, 100,000, 42,000, and 2,100 daltons. Extraction of the caprine dialysate with 100% methanol or ethanol removed the early eluting components observed in the reversed phase chromatographic analysis leaving only ICPF eluting at 9.8 minutes. Size exclusion HPLC of the material extracted by alcohol revealed a single broad peak in the 2000 to 4000 MW range. This result is consistent with the HPLC-MS analysis of the caprine dialysate which indicated that the early eluting components were a mixture of low molecular weight peptides and lipopeptides (<4,000 dalton). When analyzed by size exclusion HPLC, the residue remaining after alcohol extraction continues to elute in the 870,000 to 6,000 dalton range, no components eluting in the 2,000 dalton range, retains the pattern that is similar to the native ICPF dialysate, and contains only the single component eluting at ~9.8 minutes by reversed phase HPLC. A comparison of the reversed phase HPLC before and after alcohol extraction is presented in FIG. 10. Identical results were obtained after the preparative scale isolation of ICPF eluting at ~9.8 minutes and reanalysis by both size exclusion HPLC and reversed phase HPLC.

Figure 11A:
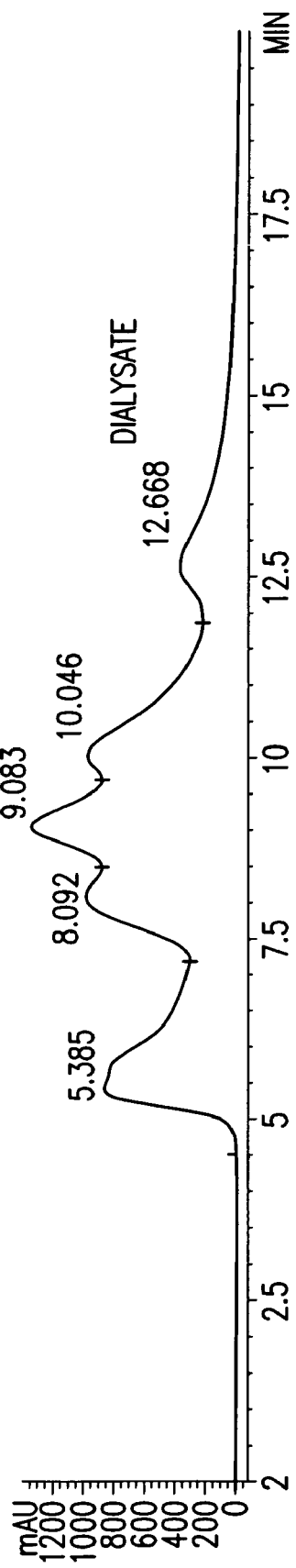
FIG. 11. A comparison of the size exclusion HPLC elution profiles at 220 nm for ICPF fractions obtained during ultrafiltration and ICPF prepared by dialysis.
Figure 11A:
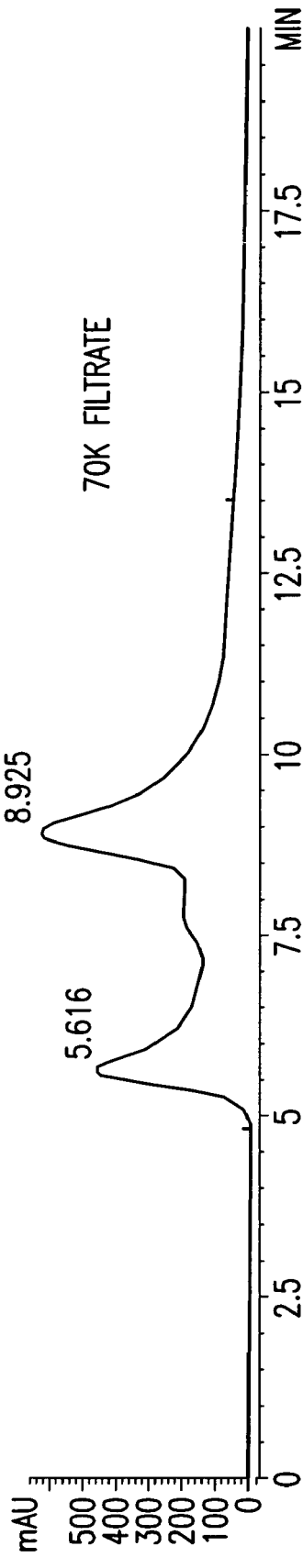
Figure 11B:
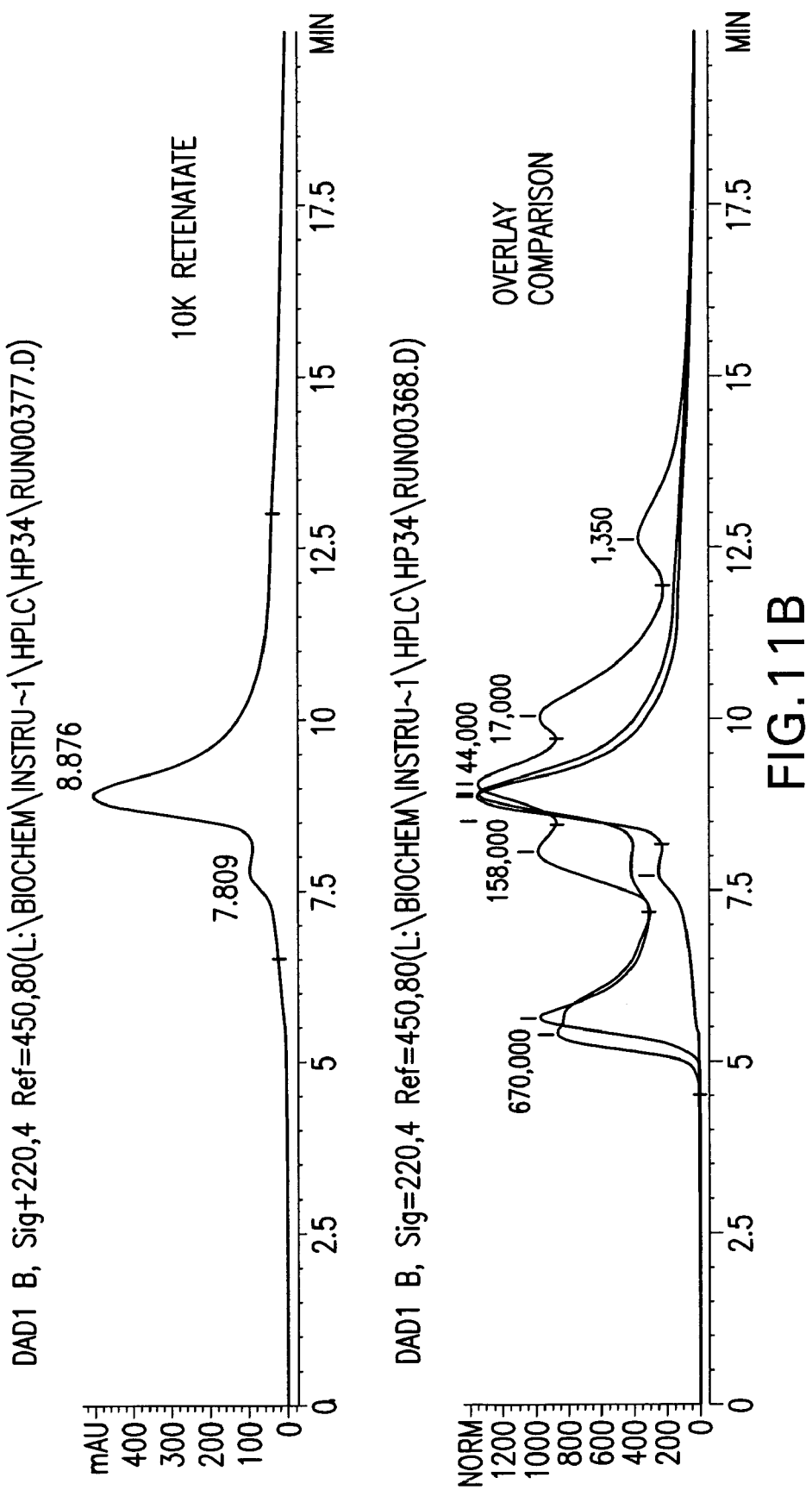

A comparison of the size exclusion HPLC results for ICPF obtained by dialysis to the fractions obtained by ultrafiltration clearly indicates that the 10 kDa retentate is enriched with the fraction eluting at nominally 44,000 dalton. Bioassay of the fractions obtained from ultrafiltration indicated the biologically active component (ICPF) to be in the 10 kDa retentate. These results are presented in FIG. 11.

Figure 12A:
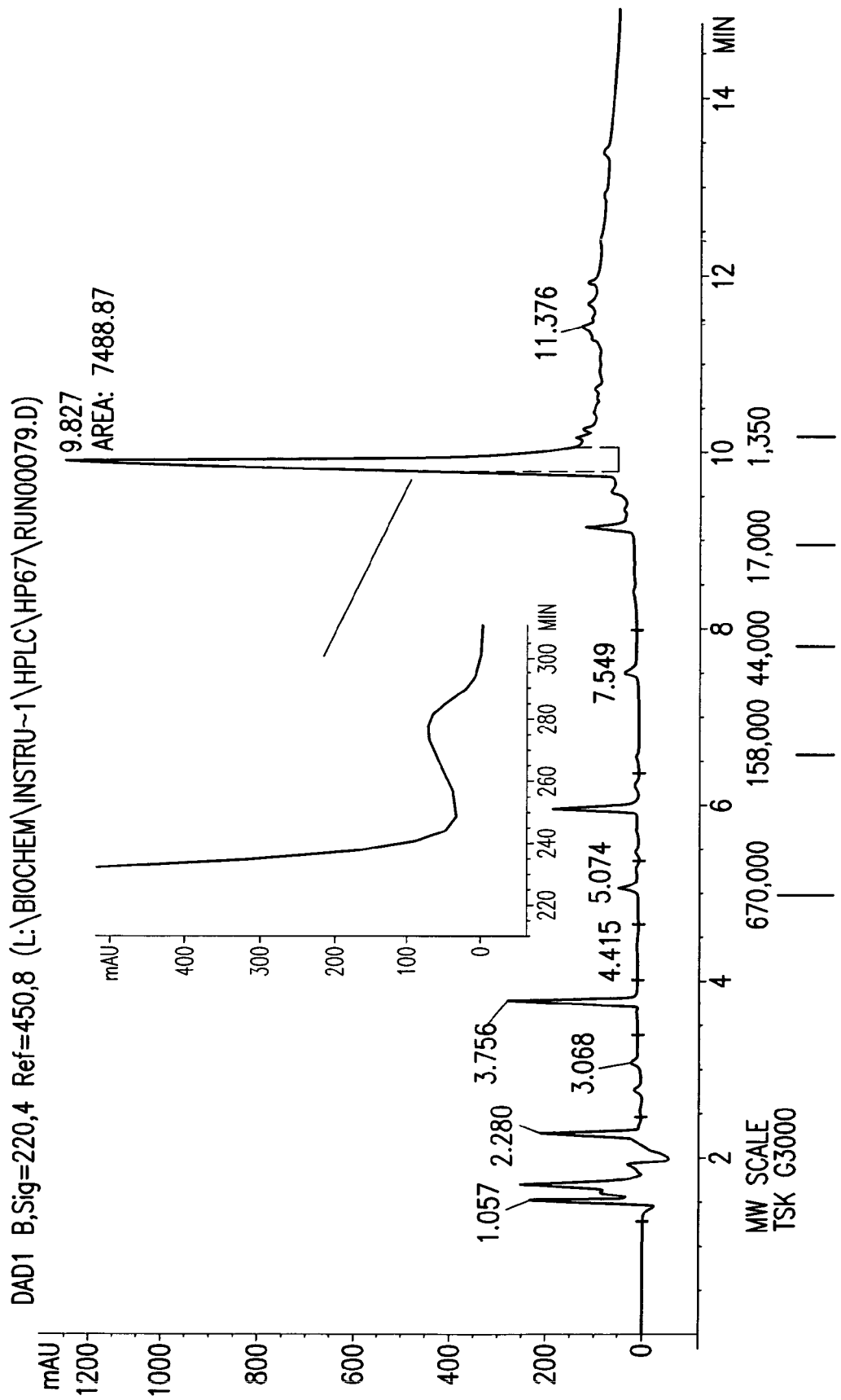
FIG. 12. A comparison of the total UV spectra of ICPF obtained from reversed phase HPLC (top) with the UV spectra obtained at different time points during the size exclusion HPLC elution profile of ICPF (bottom). The low molecular weight fraction (~1,500 amu {atomic mass units}) was previously shown to be comprised of the early eluting components from reversed phase HPLC.
Figure 12B:
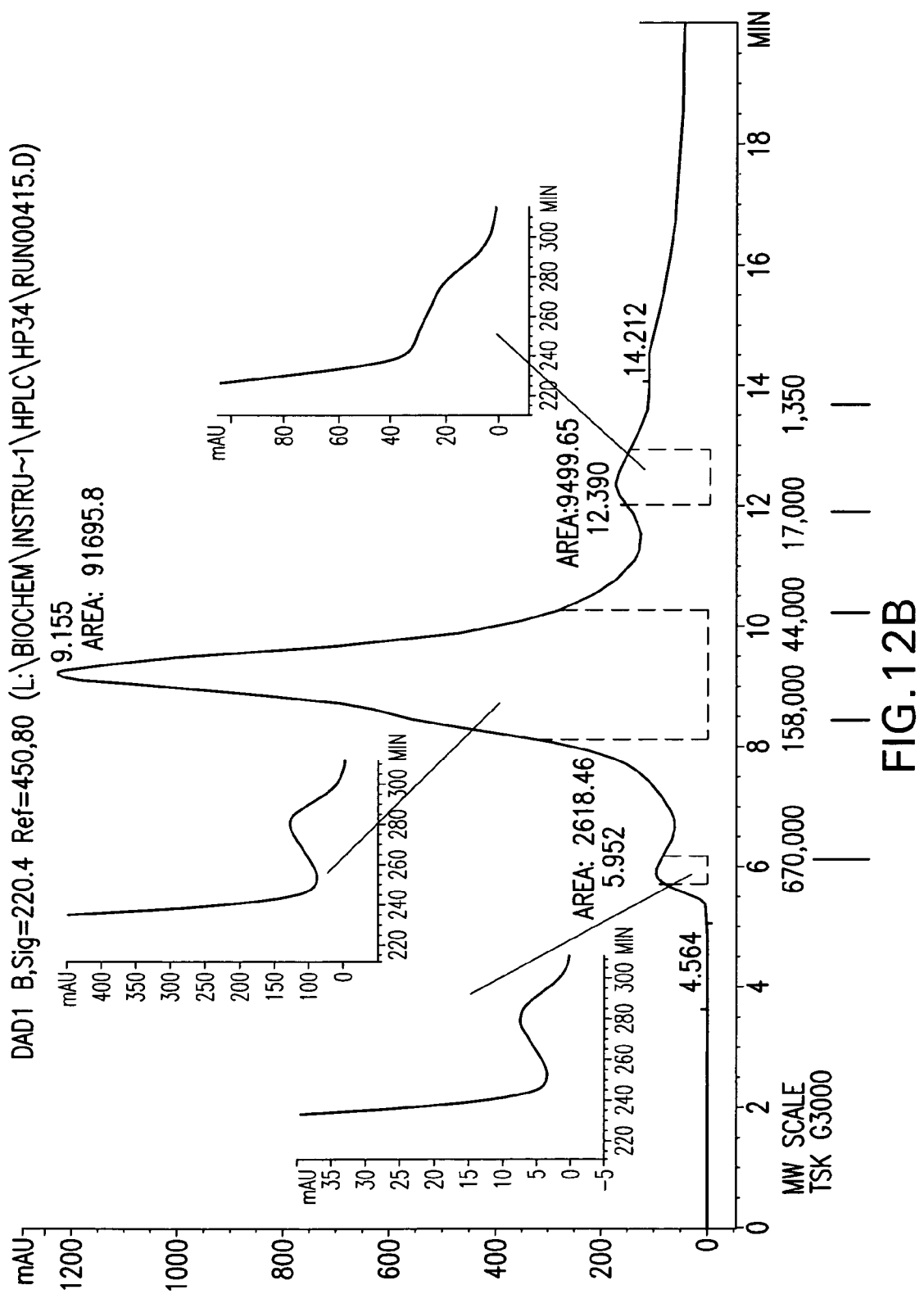
Figure 13:
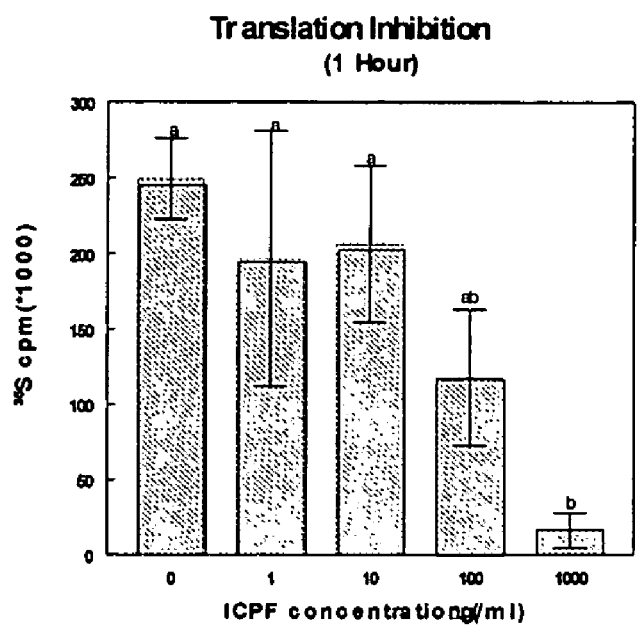
FIG. 13. Human diploid fibroblast cells were incubated with S$^{35}$ labeled methionine and varying concentrations of ICPF (1 μg/ml to 1,000 μg/ml). The incorporation of the radiolabel into the cellular proteins was measured after 1 hour (10 A) and after 24 hours (10 B). The control cells received no ICPF. The values shown are the average of replicate measurements (n=5) and the respective standard error of the mean (SEM).
Figure 13:
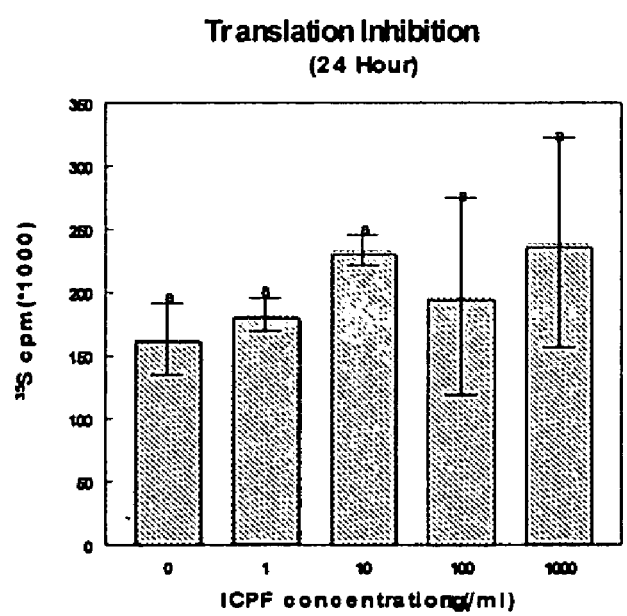

UV spectral analysis of the fractions eluting during size exclusion HPLC are virtually identical and reveal only an aromatic peptidyl chromophore that is identical to the UV spectrum of the ICPF isolated from reversed phase HPLC. The UV spectrum of the low molecular weight fraction is qualitatively different from the UV spectra of the high molecular weight components. The low molecular weight fraction has previously been shown to be distinct from ICPF and consist of the early eluting components during reversed phase HPLC that contains of a mixture of low molecular weight peptides, lipopeptides, and oligosaccharide-peptide conjugates. These results are presented in FIG. 12.

The results herein indicate that ICPF comprises a ~2,000 dalton lipopeptide that self associates into high molecular weight aggregates over the range of 900,000 to 4,000 daltons and has a median molecular weight of 44,000 dalton. This also explains the surprising observation that ICPF was not found in the 10 kDa filtrate after ultrafiltration yet ICPF is found in the dialysate when serum is dialyzed in a 10 kDa dialysis bag.

That the ultrafiltration process is a dynamic filtration process and that dialysis is an equilibrium driven osmotic process offers an explanation. During dialysis the equilibrium between dissociated and un-dissociated forms of ICPF can be established. This equilibrium will continually re-establish itself as the dissociated monomeric unit crosses the dialysis membrane into the dialysate. Upon concentration of the dialysate the aggregated form of ICPF is re-established. During ultrafiltration no such equilibrium between dissociated and undissociated forms of ICPF can be established. That this mechanism is operating here is evidenced by the observation that ICPF isolated as the monomeric unit either by preparative reversed phase HPLC or alcohol extraction will self associate to give the original size exclusion elution profile.

Our molecular modeling studies suggest that ICPF monomers will associate with the peptide orientation of C-terminus to N-terminus. This structure is stabilized by intercalation of the diacyl glycerol of one peptide with the 2-stearyl ester of the next peptide. The overall tertiary structure of the aggregated ICPF will be predominately α-helical with lipid nodes every 7 amino acids. The aggregate structure is further stabilized by hydrogen bonding between the N-terminal arginine of one peptide and the periapical arginine in the 8 position of the next peptide. This overall tertiary structure also explains the water solubility of lipopeptides like ICPF. As a monomeric unit the lipophilic character of ICPF would preclude water solubility. However, in the aggregate form, the tertiary structure concentrates the lipids as internal nodes surrounded by the hydrophilic peptide helix.

Molecular modeling studies with ICPF have also shown another unexpected and surprising result. Using MOPAC with MNDO to optimize heat of formation and MM2 to minimize steric energy while examining the likely biological derivatives of ICPF, it was discovered that if the 2-stearyl ester is removed the ε-ammonium ion of the 8 arginine is positioned to effect an intramolecular hydrogen ion transfer that will result in hydrolysis of the terminal diacyl glycerol and release the free peptide. Although only a theoretically predicted outcome, this possibility has intriguing biological implications. For instance, it is well known that early stage inflammatory processes release intracellular proteolytic and hydrolytic enzymes into the extra cellular matrix. In a model, ICPF circulates in its nascent form as the high molecular weight aggregate. Once the inflammatory extracellular matrix is encountered, the enzymatic action of lipases will cleave the free 2-stearyl ester of the N-terminal portion of the aggregate. This enables the 8-arginine to effect intramolecular hydrolysis of the diacyl glycerol and release the free peptide. This process can repeat itself to release additional peptide. The free peptide then binds to the T cell receptor and the ICPF cascade is initiated. For each mole of peptide released three moles of lipid are released and this stoichiometry conveniently accounts for the observed 'lipemia of infection'.

Product Safety

The following represents preferred product safety features of ICPF of the present invention. It is recognized by those of ordinary skill in the art from the complete disclosure and in particular the exemplars herein that additional safety features may be associated with ICPF of the invention.

Endotoxin Assay

The standardized endotoxic activity for two independent preparations of ICPF was determined by an LAL gel clot assay. The threshold sensitivity of the reaction was 0.03 endotoxic unit (EU) per ml. Each preparation had equivalent endotoxin levels of 0.08 EU/mg. ICPF does not contain a level of endotoxin sufficient to promote a pyrogenic response.

Human Fibroblast Toxicity

ICPF was prepared as a 1 mg/ml stock solution in media and was serially diluted in a decade series to give 1, 10, 100, and 1000 μg/ml test solutions. Test solutions thus prepared were used within one hour. Human diploid fibroblast cell cultures established from skin tissue were maintained in Dulbecco's modified Eagle's media (DMEM) and were transferred into 12-well culture plates at a concentration of $5\times10^4$ cells/cm$^2$ (in 2 ml media) and incubated for 24 hours at 37° C. with 5% $CO_2$. The trypan blue dye exclusion test was used as a measure of cell viability. At 24 hours, there was no difference from control wells for any of the concentrations of ICPF.

The degree of protein translation inhibition of cells exposed to ICPF was also measured as the uptake of $S^{35}$-methionine. After a 1 hour exposure to ICPF, significant translation inhibition was only noted at a test concentration of 1 mg/ml ICPF (FIG. 13 A). However after a 24 hour exposure to ICPF, translation inhibition was not noted at any of the test concentrations of ICPF (FIG. 13 B). The highest concentration of ICPF (1 mg/ml) interfered with the ability of the cell to incorporate radiolabel. However, after 24 hours equilibrium had been established and normal cell uptake of amino acids and translation into proteins was observed. Thus ICPF has no effect on protein translation over time.

Red Blood Cell Hemolysis

Hemolytic activity of ICPF at concentrations ranging from 1 μg/ml to 1 mg/ml (n=3) was measured using a 5% suspension of freshly drawn human erythrocytes, which had been washed twice in phosphate-buffered saline. After incubation at 37° C. for 30 min, the suspension was centrifuged at 10,000 g for 10 min, and the absorbance at 400 nm was measured. Complete hemolysis as a positive control was obtained by the addition of 0.2% Triton X-100. Hemolysis of red blood cells did not occur at any concentration of ICPF.

Delayed Type Hypersensitivity

Six New Zealand White rabbits (3 animals per group) received either 5 mg of ICPF in 0.25 ml Freund's Complete Adjuvant (FCA) or 0.25 ml FCA by subcutaneous injection. On days 4, 11, and 21 one rabbit from each group was selected to receive an intradermal injection of 0.1 ml (200 ug) of ICPF and sterile water (negative control) on the exposed lateral thorax. After 15-30 minutes the injection sites were observed for raised erythematous lesions (wheals) at the injection site. No wheal development was observed indicating the absence of a delayed type hypersensitivity reaction to ICPF.

Impact of ICPF

ICPF has a profound and immense potential, not only as a therapeutic agent, but also as a prophylactic agent against bacterial pathogens and viral disease agents as well as cell metastasis in neoplastic diseases. Other areas of impact from this work include:

ICPF can replace use of antibiotics as the therapeutic of choice for infectious diseases, thus reducing usage of antibiotics and decreasing pressure that drives the development of antibiotic resistant bacterial strains.

ICPF can be a new and affordable therapy for serious infectious diseases such as cholera, dysentery, and tuberculosis that are ravaging the populations of the world's developing nations.

ICPF can be used as a "prophylactic" for short term protection in a bio-terrorism arena or other contagion environs.

ICPF can be administered as a "prophylactic" to patients undergoing major surgery to prevent post-operative infection.

ICPF can provide "long-term" protection as a vaccine adjuvant.

ICPF can be used as a safe and effective therapeutic for the prevention and treatment of seasonal influenza outbreaks.

ICPF can be used adjunctively with other therapeutic agents for the treatment of drug resistant infections.

ICPF can be used to "scavenge" metastatic cells in patients undergoing chemotherapy or surgery for the treatment of neoplastic diseases.

The impact of ICPF is far reaching and may in fact represent one of the most significant advances for treatment and prevention of infectious diseases since the discovery of penicillin and the development the Salk vaccine.

The following examples illustrate embodiments of the invention, but should not be viewed as limiting the scope of the invention.

PROPHYLACTIC AND THERAPEUTIC EXAMPLES

The breadth of the prophylactic and therapeutic efficacy of ICPF is demonstrated by the prevention and treatment of diseases of bacterial and viral origin as well as the prevention of cell metastasis in neoplastic diseases as described in the following examples.

Example 1

Prevention of Bacterial Diseases

Typhoid Fever

Figure 14:
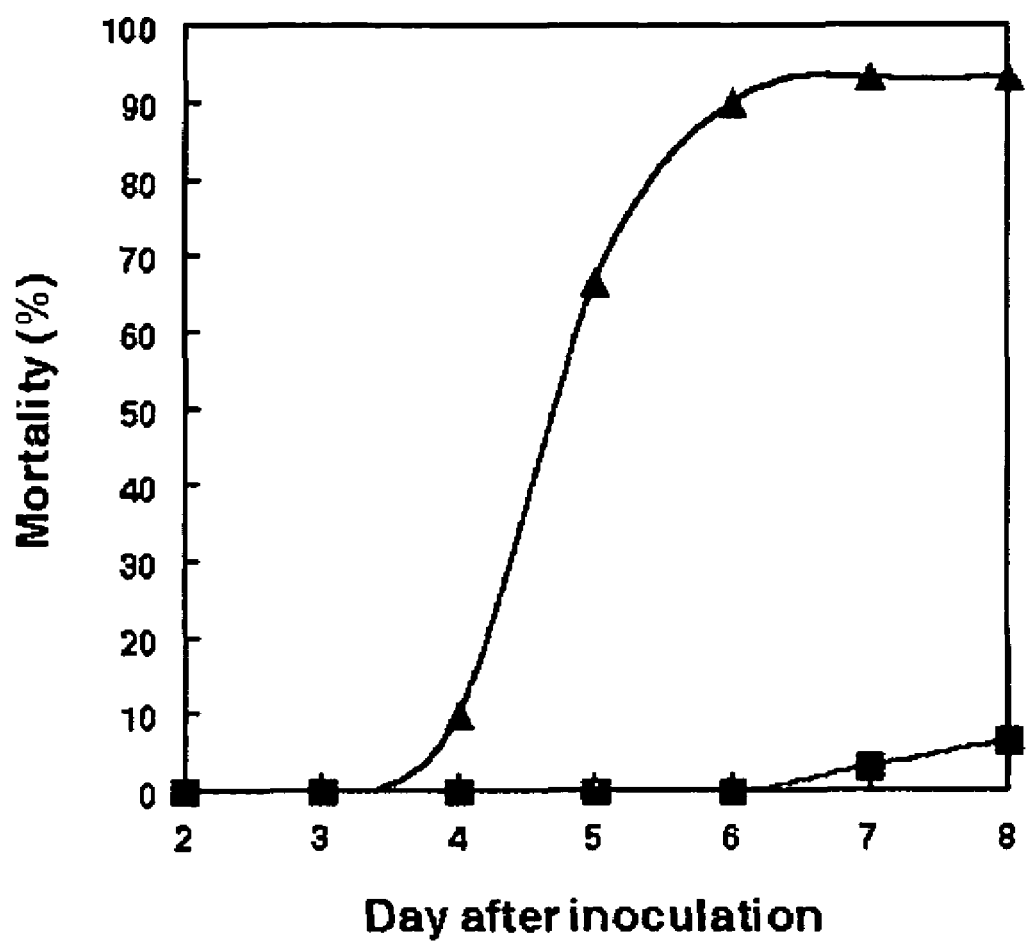
FIG. 14. Control mice were administered 0.1 ml (~5×10$^3$ cfu {colony forming units}) of S. typhimurium i.p. on day 0 (▲), while treated mice received both S. typhimurium on day 0 and a 0.25 ml subcutaneous injection of ICPF (5 mg) on day −1 (■). Each data point represents the average daily mortality (n=5) with its associated standard experimental error per cage of 5 mice.

*Salmonella typhimurium* is a gram negative organism that causes an intracellular infection in its host. The murine salmonellosis model is a well-accepted animal model for human typhoid fever. The efficacy of the ICPF fraction was clinically assessed by monitoring mortality in female Swiss Webster mice challenged with *Salmonella typhimurium*. In mice, host-adapted *Salmonella* can invade and multiply in the tissues of the reticuloendothelial system, with the severity and outcome of the disease depending on the infecting dose, on the virulence of the bacterial strain, and on the genetic background of the animal (Mastroeni, 1999). We observed a significant reduction in mortality in challenged mice that received ICPF (p<0.05). Control mice experienced 90% mortality 8 days after receiving the bacterial challenge while mice treated with 5 mg ICPF one day prior to challenge presented only 10% mortality. The results are depicted in FIG. 14. The reduction of mortality correlated with a suppressed bacterial population (as detected in the spleen) between control and ICPF treated mice. No therapeutic benefit was provided to mice undergoing salmonellosis when treated with 5 mg of purified caprine immunoglobulin (IgG).

Example 2

Treatment of Established Bacterial Infections

Bacterial Mastitis

The efficacy of ICPF was examined in the treatment of bovine mastitis, a multi-factorial bacterial infection. Forty-nine animals (n=49) with an elevated somatic cell count (SCC) and not undergoing treatment were randomly selected and treated with ICPF (60 mg, i.m.) followed by a second booster injection three days after the initial dose. The remainder of the herd (n=100), excluding animals undergoing treatment, were left untreated as a control group. The somatic cell count (SCC) of the treatment group animals and the control animals were compared thirty days later. The test and control groups were determined not to be statistically different prior to treatment (t=0.1703, P=0.8650). After treatment fifty-six percent (56%) of the animals in the ICPF treatment group showed a decreased SCC with an average SCC decrease of 25% per animal while the average SCC in the untreated control animals increased by 11% per animal over the test period. This difference was determined to be statistically significant (P<0.05).

Nineteen animals were showing signs of clinical mastitis, i.e. abnormal milk appearance, painful teat, etc. These animals were randomly assigned to either a test or a control group. The control group animals (n=10) were treated according to the dairy's normal practice for treatment of clinical cases of mastitis, i.e. intramuscular injection of Polyflex brand (Fort Dodge Animal Health) of ampicillin (5 mg/lb×3 days). The test group (n=9) animals were treated with ICPF (60 mg, i.m.) followed by a booster injection three days later. The SCC's for the treatment and control animals were compared 30 days later. The means of the pre-treatment test and control groups were determined to not be statistically different and neither were the standard deviations of the two groups statistically different. Seven animals in the test group showed improvement and the average SCC for the group declined by 19%. Two animals in the test group were refractory to treatment. Only one animal in the control group showed improvement and the average somatic cell count for the control group increased by 7% during the test period.

Figure 15:
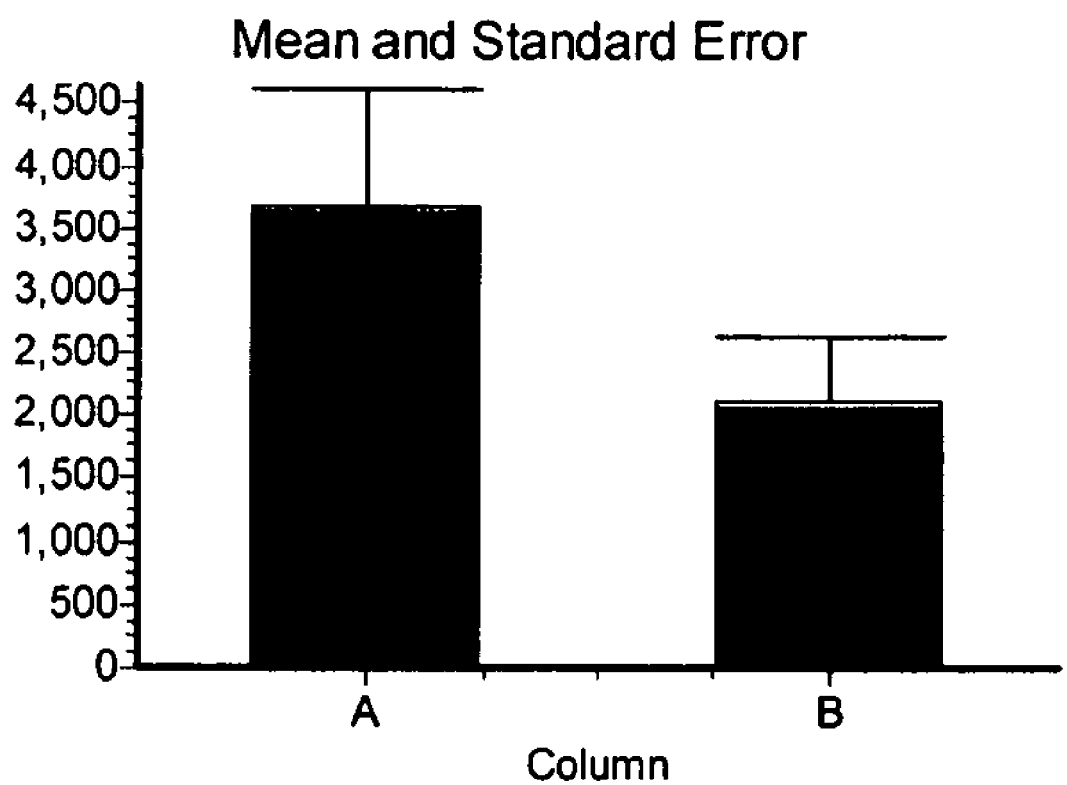
FIG. 15. Efficacy of ICPF used adjunctively with antibiotic (Polyflex brand of ampicillin) in the treatment of refractory cases of mastitis. Column A is the pre-treatment Mean Somatic Cell Count and Standard Error of the Mean (SEM). Column B is the post-treatment Mean Somnatic Cell Count and Standard Error of the Mean.

Nine animals in the herd were historically refractory to antibiotic treatment or had multiple incidences of clinical mastitis while in milk. These nine animals plus the two refractory animals from the ICPF Test Group were grouped together (n=11) for treatment with antibiotic (Polyflex) plus ICPF as an adjunctive therapeutic. After the next scheduled SCC measurement, the treatment efficacy was evaluated. Eight of the 11 ICPF Test Group animals improved (80%) with a 42% decrease in this group's average SCC. Two animals (20%) remained refractory to treatment. These results are presented in FIG. 15.

Figure 16:
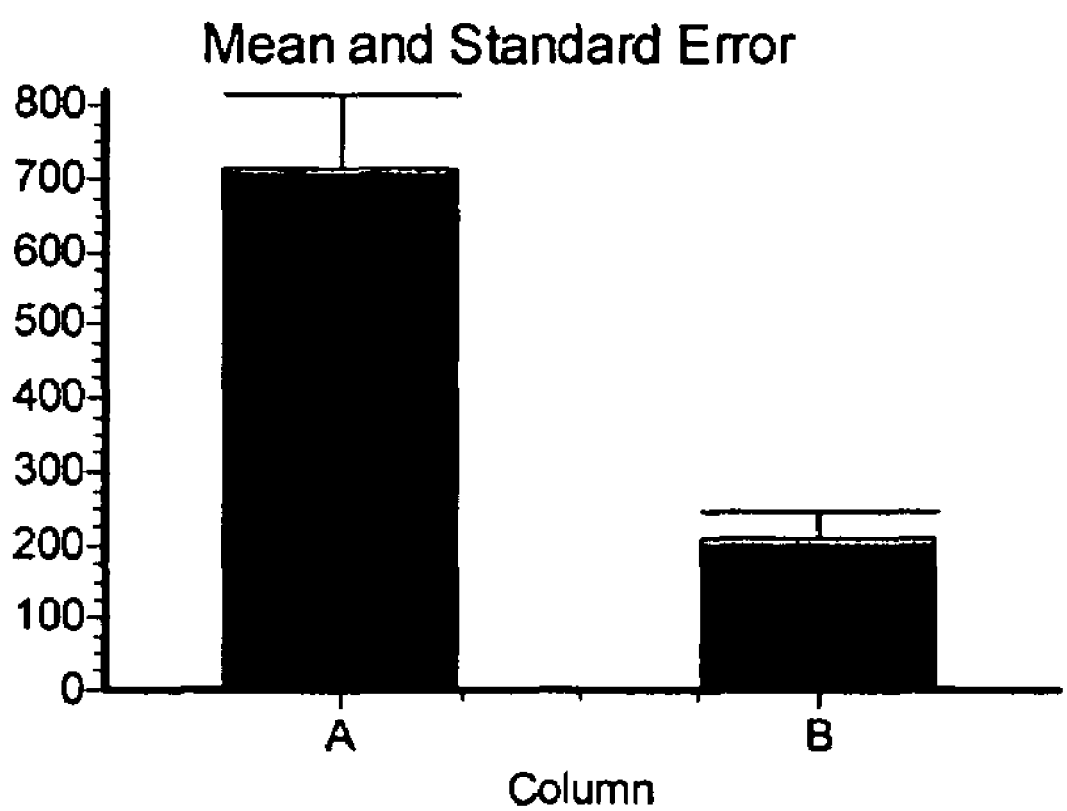
FIG. 16. A comparison of the mean and standard error of the mean for the efficacy of ICPF treatment of sub-clinical cases of mastitis. Column A is the pre-treatment somatic cell count (SCC) and Column B is the post-treatment SCC.

Five animals were diagnosed with sub-clinical cases of mastitis. Bacterial cultures of the milk from these five animals showed a mixture of non-hemolytic *Streptococcus* and *E. coli* as the causative organisms. These five sub-clinical animals were treated with ICPF and the SCC's were measured 30 days after treatment. Four of the five animals had SCC's that were normal after treatment and all five animals showed improvement. The average SCC for this group before treatment was 715,000 and after treatment declined to 205,000. A two-tailed t-test for significance with Welch's approximation to correct for the unequal standard deviations indicated that the difference in the means of the pre-treatment and post-treatment groups was very significant (P=0.005, t=4.759). The results are presented below in FIG. 16.

Example 3

Treatment of Established Viral Infections

Parvovirus

Parvovirus is representative of the single stranded DNA class of viruses. A comparative study was performed to determine whether survival of parvoviral enteritis could be increased when conventional supportive therapy (as directed in a clinical environment) was augmented with an immunotherapeutic approach. Immunostimulation was initiated by the subcutaneous administration of 5 mg of immune cell proliferation factor (ICPF). The integrity of the study was maintained by blinding the attending veterinarian to the identity of the biological response modifier or placebo.

The symptomology of a parvoviral infection may progress rapidly from mild depression and refusal of food to acute vomiting, diarrhea, hemorrhagic gastroenteritis, shock-like collapse and death. Upon diagnosis and entry into the study all animals were placed in an isolation unit and intravenously provided cefazolin (30 mg/kg every 8 hours)—to combat bacterial infection, metoclopramide [Reglan®] (0.6 mg/kg every 8 hours)—to normalize stomach contraction and reduce nausea, and 5% dextrose lactated Ringers solution—a physiologic electrolyte solution used to restore fluid and electrolyte balance.

Dogs diagnosed with parvoviral enteritis were randomly assigned to either the placebo (n=25) or ICPF (n=25) treatment group. ICPF (1 ml, 5 mg/ml) was administered subcutaneously. Mortality dropped significantly (p=0.0101) from 68 percent in the placebo group to 32 percent in the ICPF treated group.

West Nile Virus

West Nile Virus is a representative of the single stranded RNA class of viruses. Fifteen horses diagnosed with West Nile viral encephalitis were admitted to the Illinois Large Animal Clinic during the summer months of 2002. Ten animals were treated with supportive therapy (fluids, steroids) alone and seven of these animals expired (70% mortality). Five animals were treated with ICPF (50 mg, i.m.) at admission and also received the standard supportive therapy. A second dose of ICPF was administered 3 days after the first dose. Of these five animals receiving ICPF in addition to the supportive therapy only 1 animal died (20% mortality) that was recumbent upon admission.

Example 4

Prevention of Cell Metastasis in Neoplastic Diseases

Melanoma

The murine B16F10 melanoma model is a well described animal model for human melanoma. Female B6C3F1 mice were injected with B16F10 melanoma cells at a dose of $8 \times 10^5$ cells/mouse. Visual examination of the lungs after a two week incubation period showed that control mice (n=4) had blackened lungs with nodules too numerous to count through simple inspection. The lung samples obtained from control and ICPF treated mice (5 mg on day −1) were subsequently analyzed with the aid of a computerized imaging system. Tumor morphometric analysis showed that 53±10% of the lung surface from control mice was cancerous. Prophylactic administration of ICPF lowered this value to 30±9%, a statistically significant decrease (p=0.014). When this experiment was repeated with an eight fold reduction in the number of B16F10 melanoma cells, the number of melanoma nodules established on the lung surface could be established through microscopic examination. Control mice (n=10) had an average of 88±7 tumor nodules on their lungs, whereas ICPF-treated mice (n=8) had 44±11 tumor nodules, a statistically significant two fold reduction (p=0.0036).

Other embodiments and uses of the invention will be apparent to those skilled in the art from consideration of the specifications and practice of the invention disclosed herein. All U.S. patents and other documents cited herein are specifically incorporated by reference. It is intended that the specifications and examples be considered exemplary only, with the true scope and spirit of the invention being indicated by the following claims.

REFERENCES

Beutler B., and A. Cerami, 1986. Cachectin/Tumor necrosis factor: an endogenous mediator of shock and inflammation. *Immunology Research* 5:281-293.

Carding, S. R. and P. J. Egan, 2002. γδ T cells: functional plasticity and heterogeneity. *Nat. Rev. Immunol.* 2:336-345.

Chang, C. J., T. T. Chen, B. W. Cox, G. N. Dawes, W. Stemmer, J. Punnonen, and P. A. Patten, 1999. Evolution of a cytokine using DNA family shuffling. *Nature Biotechnology* 17:793-797.

Cohen M. H., P. B. Chretien, D. C. Ihde, B. E. Fossieck, R. Makuch, P. A. Bunn, A. V. Johnston, S. E. Shackney, M. J. Matthews, S. D. Lipson, D. E. Kenady, and J. D. Minna, 1979. Thymosin fraction V and intensive combination chemotherapy. Prolonging the survival of patients with small-cell lung cancer. *JAMA: The Journal of the American Medical Association* 241:1813-1815.

Cross, A. S., J. C. Sadoff, N. Kelly, F. Bernton, and P. Gemski, 1989. Pretreatment with recombinant murine tumor necrosis factor α/cachectin and murine interleukin 1α protects mice from lethal bacterial infection. *Journal of Experimental Medicine* 169:2021-2027.

Czuprynski, C. J., and J. F. Brown, 1987. Recombinant murine interleukin-1α enhancement of nonspecific antibacterial resistance. *Infection and Immunity* 55:2061-2065.

Dardenne, M., and W. Savino, 1992. Neuroendocrine circuits controlling the physiology of the thymic epithelium. *Annals of the New York Academy of Science* 650:85-90.

de Gruyter, W., 1997. Concise Encyclopedia of Biochemistry and Molecular Biology. New York. Walter de Gruyter & Co.

Diasio R. B., and A. F. LoBuglio. 1995. Immunomodulators: immunosuppressive agents and immunostimulants. In Hardman, J. G, Limbird, L. E. (eds): Goodman and Gilman's The Pharmaceutical Basis of Therapeutics, 9$^{th}$ edition, pp 1291-1308. New York, McGraw-Hill.

Dinarello, C. A., 1984. Interleukin-1 and the pathogenesis of the acute phase response. *The New England Journal of Medicine* 311:1413-1418.

Eglezos, A., P. V. Andrews, R. L. Boyd, and R. D. Helme, 1991. Modulation of the immune response by tachykinins. *Immunology and Cell Biology* 69:285-294.

Folkman, J., 1999. Angiogenic zip code. *Nature Biotechnology* 17:749.

Ford, R. B., 1986. Biological response modifiers in the management of viral infections. *Vet Clin North Am Small Animal Prac* 16:1191-1204.

Hamm, D., K. O. Willeford, G. White, S. M. Reed, and J. Hamm, 2002. Caprine serum fraction immunomodulator as supplemental treatment of lower respiratory disease in the horse. *Equine Veterinary Journal*, 34:71-75.

Hancock, R. E. W., 1997. Peptide antibiotics. *Lancet* 349: 418-422.

Hancock, R. E. W., 1999. Host defense (cationic) peptides. *Drugs* 57:469-473.

Heinrich, P. C., J. C. Castell, and T. Andus, 1990. Interleukin-6 and the acute phase response. *Biochemistry Journal* 265:621-636.

Kogut, M. H., 2000. Cytokines and prevention of infectious diseases in poultry: a review. *Avian Pathology* 29:395-404.

Kruth, S. A. 1998. Biological response modifiers: interferons, interleukins, recombinant products, liposomal products. *Vet Clin North Am Small Animal Pract* 28:269-295.

Ladel, C. H., et al., 1996. Control of natural killer cell-mediated innate resistance against the intracellular pathogen *Listeria monocytogenes* by γδ T lymphocytes. *Infect. Immun.* 64:1744-1749.

Latham, P. W., 1999. Therapeutic peptides revisisted. *Nature Biotechnology* 17:755-757.

Mackaness, G. B., 1969. The influence of immunologically committed lymphoid cells on macrophage activity in vivo. *Journal of Experimental Medicine* 129:973-992.

Maggio, J. E., 1990. Tachykinins. *Annual Review of Neuroscience* 11:13-28.

Mastroeni, P., S. Clare, S. Khan, J. A. Harrison, C. E. Hormaeche, H. Okamura, M. Kurimoto, and G. Dougan, 1999. Interleukin 18 contributes to host resistance and gamma interferon production in mice infected with virulent *Salmonella typhimurium*. *Infection and Immunity* 67:478-483.

Mizuno, T., G. Wang, J. Zhang, H. Kawagishi, T. Nishitoba, and J. Li, 1995. Reishi, *Ganodenna Lucidum* and *Ganoderma Tsugae*: Bioactive substances and medicinal effects. *Food Reviews International* 11: 151-166.

Molloy, R. G., J. A. Mannick, and M. L. Rodrick, 1993. Cytokines, sepsis, and immunomodulation. *British Journal of Surgery* 80:289-297.

Morrissey, P. J., and K. Charrier, 1994. Treatment of mice with IL-1 before infection with increases resistance to a lethal challenge with *Salmonella typhimurium*. *Journal of Immunology* 153:212-219.

Parker, T. A., K. O. Willeford, S. Parker, and K. Buddington, 2002. Reducing mortality in *Salmonella typhimurium* infected mice with a caprine serum fraction. *Antimicrobial Agents and Chemotherapy*, 46:1971-1973.

Pecyk, R. A., E. B. Fraser-Smith, and T. R. Matthews, 1989. Efficacy of interleukin-1α against systemic *Candida albicans* in normal and immunosuppressed mice. *Infection and Immunity* 57:3257-3258.

Poquet, et al., 1998. Expansion of Vγ9Vδ2 T cells is triggered by *Francisella tulerensis*-derived phosphoantigens in tularemia but not after tularemia vaccination. *Infect. Immun.* 66:2107-2114.

Rush, B. R, 2001. Clinical use of immunomodulatory agents. *Equine Veterinary Education* February, 60-68.

Rush, B. R., and M. J. Flaminio, 2000. Immunomodulation in horses. *Veterinary Clinics of North America: Equine Practice* 16:183-197.

Sanglier, J., H. Haag, T. Huck, and T. Fehr, 1993. Novel bioactive components from Actinomycetes: A short review (1988-1992). *Research in Microbiology* 144:633-642.

Shen, H., C. M. Tato, and X. Fan, 1998. *Listeria monocytogenes* as a probe to study cell-mediated immunity. *Current Opinion in Immunology* 10:450-458.

Takx-Kohlen, B. C., 1992. Immunomodulators: Future prospects. *Pharmaceutisch weekblad, Scientific edition* 14:245-52.

Tizard, I. R. 1996. Veterinary Immunology: An Introduction, 5th ed. Philadelphia, Pa.: W. B. Saunders Company.

Waage, A., R. Shalaby, and E, Terje. 1992. Tumour necrosis factor, interleukin-1, interleukin-6, interleukin-8, and interferone-G in septic shock. In: Kunkel, S. L., D. G. Remick (eds) Cytokines in health and diseases. Marcel Dekker, New York, pp 151-164.

Werner, G. H. and A. Zerial. 1984. Immunopotentiating substances with antiviral activity. 1984. In Shugar D. (ed): Viral Chemotherapy, vol 1, pp 511-599. New York, Pergamon Press.

Willeford, K. O., T. A. Parker, E. D. Peebles, C. Wang, and E. W. Jones. 2000. Reduction of mortality in specific-pathogen-free layer chickens by a caprine serum fraction after infection with *Pasteurella multocida*. *Poultry Science*, 79:1424-1429.

The invention claimed is:
1. An isolated peptide having an amino terminus and a carboxy terminus comprising:
   a sequence that consists of the sequence of SEQ ID NO 3, and
   a plurality of fatty acids, each of which is coupled to an amino acid of said sequence,
   wherein said peptide, when administered to a patient, increases the effective innate immune system response of said patient.

2. The isolated peptide of claim 1, which further comprises an arginine at the amino terminus.

3. The isolated peptide of claim 1, which further comprises a phenylalanine at the carboxy terminus.

4. The isolated peptide of claim 1, wherein the effective innate immune system response is selected from the group consisting of up-regulation of cytotoxic or phagocytic immune cells, macrophage activation, natural-killer cell activation, T-cell activation, acute-phase protein production, initiation of an inflammation cascade, antibody production, and combinations thereof.

5. The isolated peptide of claim 4, wherein the plurality of fatty acids includes at least one unsaturated fatty acid.

6. The isolated peptide of claim 4, wherein each of the fatty acids of said plurality are selected from the group consisting of stearic acid, arachidic acid, arachadonic acid, and combinations thereof.

7. The isolated peptide of claim 1, which comprises a nonapeptide.

8. The isolated peptide of claim 1, comprising the sequence of SEQ ID NO 2.

9. The isolated peptide of claim 8, wherein $X_1$ and $X_2$ of SEQ ID NO 2 wherein $X_1$ of SEQ ID NO 2 is phenylalanine and $X_2$ of SEQ ID NO 2 is serine are derivatized amino acids.

10. The isolated peptide of claim 9, which further comprises a serine-O-fatty acid ester.

11. The isolated peptide of claim 1, which comprises the sequence of SEQ ID NO 5.

12. The isolated peptide of claim 11, which further comprises up to three fatty acids, at least one of which is an unsaturated fatty acid, wherein each of the up to three fatty acids are selected from the group consisting of stearic acid, arachidic acid, arachadonic acid, and combinations thereof.

13. An isolated peptide which consists of the chemical structure as depicted in FIG. 5, wherein the structure comprises the amino acid sequence of SEQ ID NO:1 and wherein $R_1$, $R_2$ and $R_3$ represent fatty acid groups selected from the group consisting of stearic acid, arachidic acid, and arachadonic acid.

14. The isolated peptide of claim 13, which is obtained from the serum of a mammal.

15. The isolated peptide of claim 14, wherein the mammal is a horse, a goat or a human.

16. An isolated peptide consisting of the sequence of SEQ ID NO 1, SEQ ID NO 2, SEQ ID NO 3, or SEQ ID NO 5, wherein at least one amino acid of said sequence is coupled to a fatty acid, and said peptide is isolated from a mammal by a method comprising either:
dialyzing serum obtained from the mammal with a 6-10 kD cut-off dialysis membrane to produce a dialysate; and separating from said dialysate a fraction that elutes between 40 kD and 50 kD; or
passing serum obtained from the mammal through a 70 kD to 100 kD cut-off ultrafiltration membrane to produce a filtrate; and isolating a fraction from said second retentate that has a median molecular weight of between 40 kD and 50 kD; and
said peptide, when administered to a patient at a therapeutic dosage, increases the effective innate immune system of said patient.

17. The isolated peptide of claim 16, wherein at least three fatty acids are each covalently coupled to an amino acid of said sequence.

18. The isolated peptide of claim 16, wherein the mammal is a horse, goat or a human.

19. A pharmaceutical composition comprising the isolated peptide of claim 1 and a pharmaceutically acceptable carrier.

20. The pharmaceutical composition of claim 19, wherein the pharmaceutically acceptable carrier is selected from the group consisting of water, an oil, an alcohol, glycerol, or a combination thereof.

21. The pharmaceutical composition of claim 19, which does not contain sufficient endotoxin to promote a pyrogenic response.

22. The pharmaceutical composition of claim 19, wherein said composition has low toxicity and a low incidence of side effects when administered to a patent at a therapeutic dosage.

23. The pharmaceutical composition of claim 19, wherein said composition is free from contaminants and toxins.

24. The pharmaceutical composition of claim 19, which stimulates the innate immune response of a patient when administered to said patient at a therapeutic dosage.

25. An isolated peptide comprising:
a sequence consisting of SEQ ID NO 1, SEQ ID NO. 2 wherein $X_1$ of SEQ ID NO 2 is phenylalanine and $X_2$ of SEQ ID NO 2 is serine, or SEQ ID NO. 3; and
a plurality of fatty acids each covalently attached to an amino acid residue of said sequence.

26. The peptide of claim 25, wherein each fatty acid of the plurality is selected from the group consisting of stearic acid, arachidic acid, and arachadonic acid.

27. The peptide of claim 25, wherein the plurality comprises up to three.

28. The peptide of claim 26, wherein the sequence is SEQ ID NO. 2 and position $X_1$ and $X_2$ is each a derivatized or a non-derivatized amino acid.

29. The peptide of claim 28, wherein $X_2$ is serine-o-fatty acid ester.

30. The peptide of claim 25, which increases effective innate immune-system response when administered to a patient.

31. The peptide of claim 30, wherein the effective innate immune response is selected from the group consisting of up-regulation of cytotoxic or phagocytic immune cells, macrophage activation, natural-killer cell activation, T-cell activation, acute-phase protein production, initiation of an inflammation cascade, antibody production, and combinations thereof.

32. An isolated peptide comprising:
a sequence consisting of SEQ ID NO 3; and
up to three fatty acids selected from the group consisting of stearic acid, arachidic acid and arachadonic acid that are covalently linked to one or more of the amino acids of said sequence.

33. The peptide of claim 32, which, when administered to a patient, increases the effective innate inimune system response of said patient.

34. The peptide of claim 33, wherein the effective innate immune response is selected from the group consisting of up-regulation of cytotoxic or phagocytic immune cells, macrophage activation, natural-killer cell activation, T-cell activation, acute-phase protein production, imtiation of an inflammation cascade, antibody production, and combinations thereof.

* * * * *

SEQUENCE LISTING

```
<160> NUMBER OF SEQ ID NOS: 5

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: see specification as filed for preferred
      embodiments

<400> SEQUENCE: 1
```

```
Arg Ser Val Ser Leu Ser Tyr Arg Phe
  1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (9)
<223> OTHER INFORMATION: Variable amino acid

<400> SEQUENCE: 2

Arg Xaa Val Ser Leu Ser Tyr Arg Xaa
  1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Ser Leu Ser Tyr Arg
  1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: octanoyl modified

<400> SEQUENCE: 4

Gly Ser Ser Phe Leu Ser Glu
  1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ser Val Ser Leu Ser Tyr Arg Phe
  1               5
```